United States Patent [19]
Batt et al.

[11] Patent Number: 5,523,408
[45] Date of Patent: Jun. 4, 1996

[54] 2-CARBOCYCLIC AND 2-HETEROCYCLIC QUINOLINE-4-CARBOXYLIC ACIDS AND SALTS THEREOF USEFUL AS IMMUNOSUPPRESSIVE AGENTS

[75] Inventors: Douglas G. Batt, Wilmington, Del.; Joseph J. Petraitis, Glenmoore, Pa.; Susan R. Sherk, Wilmington, Del.

[73] Assignee: The Dupont Merck Pharmaceutical Company, Wilmington, Del.

[21] Appl. No.: 217,911

[22] Filed: Mar. 25, 1994

[51] Int. Cl.$^6$ .................... C07D 401/04; C07D 417/14; C07D 413/14; A61K 31/47; A61K 31/495; A61K 31/535

[52] U.S. Cl. .................... 546/167; 546/170; 544/128; 544/363

[58] Field of Search .................... 546/167, 170; 544/128, 363; 514/233.5, 255, 314

[56] References Cited

U.S. PATENT DOCUMENTS 4,680,299  7/1987  Hesson .................... 514/311

FOREIGN PATENT DOCUMENTS

92/20642  of 0000  WIPO.

*Primary Examiner*—David B. Springer
*Attorney, Agent, or Firm*—Karen H. Kondrad; Blair Q. Ferguson

[57] ABSTRACT

This invention relates to 2-carbocyclic and 2-heterocyclic quinoline-4-carbocyclic acid compounds, and salts thereof, to pharmaceutical compositions comprising such compounds, and to methods of using such compounds for the treatment and/or prevention of organ transplantation rejection, graft versus host disease, and chronic inflammatory diseases, including but not limited to psoriasis and rheumatoid arthritis, in a mammal.

8 Claims, No Drawings

2-CARBOCYCLIC AND 2-HETEROCYCLIC QUINOLINE-4-CARBOXYLIC ACIDS AND SALTS THEREOF USEFUL AS IMMUNOSUPPRESSIVE AGENTS

FIELD OF THE INVENTION

This invention relates to 2-carbocyclic and 2-heterocyclic quinoline-4-carboxylic acid compounds, and salts thereof, to pharmaceutical compositions comprising such compounds, and to methods of using such compounds for the treatment and/or prevention of organ transplantation rejection, graft versus host disease, autoimmune diseases, and chronic inflammatory diseases, including but not limited to psoriasis and rheumatoid arthritis, in a mammal.

BACKGROUND OF THE INVENTION

Current recommended therapy for the prevention of organ transplantation rejection and related disorders, including graft versus host disease, traditionally involves patient treatment with cyclosporin A and adjunctive therapy with corticosteroids and other immunosuppressive drugs (Jacobs and Elgin, "Cyclosporin A, Current Status, Including the Cape Town Experience" in *Immune Modulation Agents and Their Mechanisms*, ISBN 0-8247-7178-8, 1984, pp. 191-228; *Transplantation and Clinical Immunology*, Volume XX Combined Immuno-suppressive Therapy in Transplantation ISBN 0-444-81068-4, 1989).

Presently, cyclosporin A (CSA), an immunosuppressive agent, used in combination with other adjunctive therapies, such as azathioprine and corticosteroids, is the treatment of choice for the prevention of organ transplantation rejection. Other immunosuppressive agents such as azathioprine (AZA), corticosteroids (such as prednisone), OKT3, FK506, mycophenolic acid or the morpholine ethyl ester thereof, 15-deoxyspergualin, rapamycin, mizoribine, misoprostol and anti-interleukin-2 receptor antibodies, have been used or have been suggested to be useful in the treatment and/or prevention of organ transplantation rejection.

Use of any of these known immunosuppressive compounds, either alone or in combination, is associated with a high incidence of side effects such as nephrotoxicity and/or hepatotoxicity. Thus, there presently exists a need for improved therapies to replace or to be used in combination with CSA or other currently known immunosuppressive drugs for the treatment of cancer and for the treatment and/or prevention of organ transplantation rejection, graft versus host disease, autoimmune diseases, and chronic inflammatory diseases, including but not limited to psoriasis and rheumatoid arthritis.

The 2-carbocyclic and 2-heterocyclic quinolinecarboxylic acids of the present invention are potent inhibitors of dihydroorotate dehydrogenase, the fourth enzyme in the de novo pyrimidine nucleotide biosynthesis pathway, and therefore have a unique mechanism of action (inhibition of dihydroorotate dehydrogenase) which is distinct from other available immunosuppressive agents. The compounds of the present invention will be useful as single therapy agents as well as agents to be used in combination with other compounds currently used in these clinical regimens such as CSA. The compounds of the present invention should be useful to permit the administration of reduced doses of other immunosuppressive agents cyclosporin A (CSA or CsA) and analogs thereof, FK506 (or FK-506) and analogs thereof, corticosteroids, azathioprine (AZA), mycophenolic acid or the morpholine ethyl ester thereof, mycophenolate mofetil, rapamycin, 15-deoxyspergualin, mizoribine, leflunomide, OKT3, anti-interleukin-2 receptor antibodies, misoprostol, methotrexate, cyclophosphamide, and anti-lymphocyte/thymocyte serums, used in combination therewith, thereby reducing the adverse effects of these agents.

U.S. Pat. No. 4,680,299 (Hesson) discloses 2-phenyl-4-quinolinecarboxylic acids as tumor-inhibiting agents. Additional utilities for these compounds in the treatment of skin and epithelial diseases and as immunomodulatory or immunosuppressive agents are disclosed in U.S. Pat. No. 4,861,783 (Ackerman et al.) and U.S. Pat. No. 4,968,701, (Ackerman et al.). U.S. Pat. No. 5,204,329 (Ackerman et al.) describes the use of these compounds in combination with a second immunosuppressive agent for the treatment of transplantation rejection and other disease conditions.

Additional examples of 2-phenyl-4-quinolinecarboxylic acids useful in the treatment of arthritis and for inducing immunosuppression are disclosed in U.S. Pat. No. 4,847,381 (Sutherland et al.) and in U.S. Pat. No. 4,968,702 (Poletto et al.).

Buu-Hoi and Lavit [*J. Chem. Soc.*, 2412 (1956)] disclose the compound of the structure shown below. No utility is claimed.

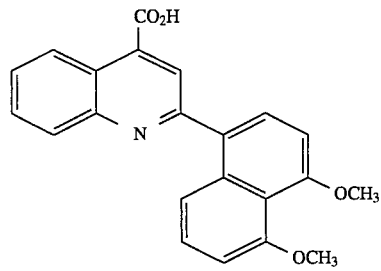

Buu-Hoi and Cagniant [Chem. Bet., 76, 1269 (1943)] describe preparation of the compound shown below. No utility is claimed.

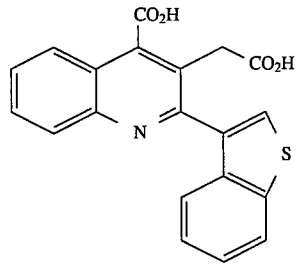

Nguyen et al. [*Tap Chi Hoa Hoc*, 27 (1), 27 (1989)]detail the preparation of the compound shown below, but claim no utility for the compound.

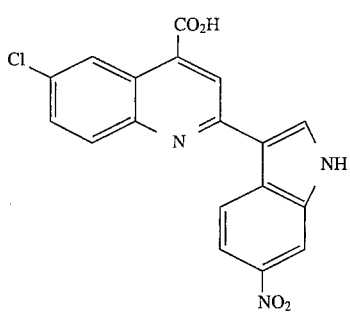

U.S. Pat. No. 3,799,929 (Holmes) describes the synthesis of the antibacterial compounds shown below, in which R is either H or methyl.

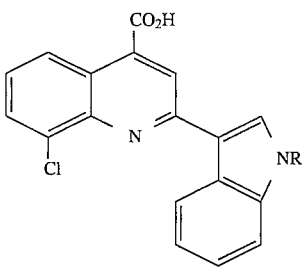

Spada et al.(WO92/20642) disclose compounds of the structure below, in which R is H or phenylsulfonyl, as effective in the treatment of psoriasis, atherosclerosis and vascular reocclusion.

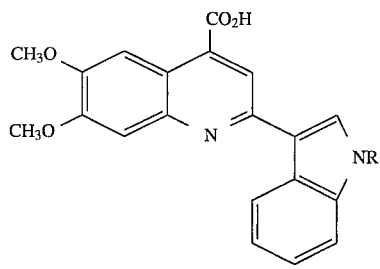

It has now been found that the carbocyclic and heterocyclic quinolinecarboxylic acid compounds described herein are useful for the treatment and/or prevention of organ transplantation rejection, graft versus host disease, autoimmune diseases, and chronic inflammatory diseases, including but not limited to psoriasis and rheumatoid arthritis, in a mammal. There are no literature references disclosing compounds of the present invention, or derivatives thereof, or their use in treating and/or preventing immunologic disorders.

The 2-carbocyclic and 2-heterocyclic quinolinecarboxylic acid compounds of this invention can be used alone or in combination with one or more additional known immunosuppressive agents, such as cyclosporin A (CSA or CsA) and analogs thereof, FK506 (or FK-506) and analogs thereof, corticosteroids, azathioprine (AZA), mycophenolic acid or the morpholine ethyl ester thereof, mycophenolate mofetil, rapamycin, 15-deoxyspergulin, mizoribine, leflunomide, OKT3, anti-interleukin-2 receptor antibodies, misoprostol, methotrexate, cyclophosphamide, and anti-lymphocyte/thymocyte serums, thereby to reduce the dosage required and associated adverse effects of these immunosuppressive agents.

The isolation of the FK506 is described in European Patent Application publication number 240,773, published Oct. 14, 1987 and the chemical synthesis of FK506 is described by Jones et al.(*J. Am. Chem. Soc.*, 111, 1157 (1989).

The preparation of azathioprine is described in U.S. Pat. No. 3,056,785 issued to Burroughs Wellcome. Azathioprine is available as Imuran®, for which the product information, including dosage and administration, is given in *Physicians'Desk Reference* 44th Edition, 1990, pp. 777–778.

The preparation of cyclosporin is described in U.S. Pat. No. 4,117,118 issued to Sandoz. Cyclosporin A is available as Sandimmune®, for which the product information, including dosage and information, is given in *Physicians'Desk Reference* 44th Edition, 1990, pp. 1950–1952.

The preparation of prednisone is described in U.S. Pat. Nos. 2,897,216 and 3,134,718 issued to Schering. Prednisone is available commercially from several manufacturers as are other corticosteroids (see generally, *Physicians'Desk Reference, supra*).

Murine monoclonal antibody to the human T3 antigen (herein referred to as OKT3) is available as Orthoclone OKT®3, for which the product information, including dosage and administration and references to methods of preparation, is given in *Physicians'Desk Reference*, 1990, pp. 1553–1554.

The preparation of mycophenolic acid is described in British Patents 1,157,099; 1,157,100; and 1,158,387 issued to ICI.

15-deoxyspergulin is a derivative of spergualin discovered in culture filtrates of the bacterial strain BGM162-aFZ as reported in Ochiai et al. Prolongation of Rat Heart Allograft Survival by 15-deoxyspergulin, *J. Antibiot.* (Tokyo), 40, 249 (1987).

Mizoribine is described in U.S. Pat. No. 3,888,843 issued to Toyo Jozo.

Misoprostol, a prostaglandin (PGE1) analog, is described in U.S. Pat. No. 3,965,143 assigned to Searle and U.S. Pat. No. 4,132,738 assigned to Miles.

Rapamycin is described in U.S. Pat. Nos. 4,650,803; 4,316,885; 4,885,171; 3,993,749 and 3,929,992, all assigned to Ayerst.

Antibodies to the IL-2 receptor protein are described in U.S. Pat. Nos. 4,578,335 and 4,845,198 (Immunex) and U.S. Ser. No. 7/341,361 and U.S. Pat. 4,892,827 issued to Pastan et al.

SUMMARY OF THE INVENTION

This invention relates to a series of novel 2-carbocyclic and 2-heterocyclic quinolinecarboxylic acid compounds and derivatives thereof, and pharmaceutical compositions comprising such compounds, and to methods of using such compounds for the treatment and/or prevention of organ transplantation rejection, graft versus host disease, autoimmune diseases, and chronic inflammatory diseases, including but not limited to psoriasis and rheumatoid arthritis, in a mammal. The compounds of the present invention are also useful for the treatment of tumors in a mammal.

There is provided by this invention a compound of the formula (I):

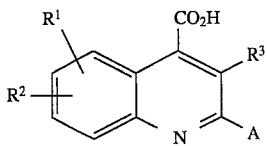

pharmaceutically acceptable salts or prodrug forms thereof wherein:

A is selected from:

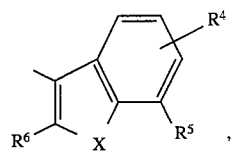

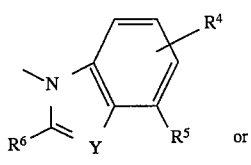

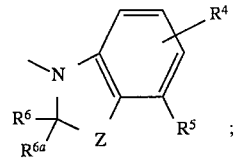

X is —N($R^7$)—, —O—, —S—, or —CH=CH—;
is —N— or —C($R^8$)—;
Z is —C($R^8$)($R^9$)—;
$R^1$ and $R^2$ are independently selected from H, Cl, Br, F, $CF_3$, or $C_1$-$C_4$ alkyl;
$R_3$ is selected from hydrogen, $C_1$-$C_3$ alkyl, —CN, —$NR^8R^9$, —$OR^8$, —$SR^8$, —$NO_2$, —$CF_3$, —$OCF_3$, —$SCF_3$;
$R^4$ is selected from hydrogen, Cl, F, $C_1$-$C_3$ alkyl, —$OR^{8a}$, —$CF_3$, —$OCF_3$, —$SR^{8a}$, —$SCF_3$, —$NR^8R^9$;
$R^5$ is an aryl or heteroaryl selected from phenyl, thienyl, furyl, pyridinyl, thiazolyl, or oxazolyl, said aryl or heteroaryl being optionally substituted with 0–2 $R^{11}$;
$R^6$ and $R^{6a}$ are independently selected from hydrogen or $C_1$-$C_3$ alkyl;
$R^7$, $R^8$, and $R^9$ are independently selected from hydrogen or $C_1$-$C_3$ alkyl;
$R^{8a}$ is $C_1$-$C_3$ alkyl;
$R^8$ and $R^9$ can alternatively join to form—($CH_2$) 4—, —($CH_2$) 5—, —$CH_2CH_2$N ($R^{10}$) $CH_2CH_2$—, or —$CH_2CH_2OCH_2CH_2$—;
$R^{10}$ is hydrogen or methyl.
$R^{11}$ is selected from hydrogen, Cl, F, $C_1$-$C_3$ alkyl, —$OR^{8a}$, —$CF_3$, —$OCF_3$, —$SR^{8a}$, —$SCF_3$, —$NR^8R^9$;

Preferred compounds of the present invention are compounds of Formula II :

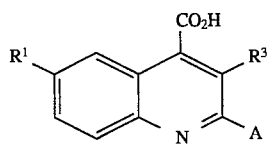

wherein:

X is —$NR^7$—or —CH=CH—;
Y is —C ($R^8$)—, or—N—;
Z is —C ($R^8$)($R^9$)—
$R^1$ is F or $CF_3$;
$R^3$ is hydrogen or methyl;
$R^4$ is hydrogen;
$R^5$ is phenyl substituted with 0–2 $R^{11}$;
$R^6$ and $R^{6a}$ are both hydrogen;
$R^8$ is H or $CH_3$;
$R^{11}$ is hydrogen, methyl, —$OCH_3$, —F or —$CF_3$;

More preferred compounds of the present invention are compounds of formula II wherein:

$R^5$ is phenyl, 2-methylphenyl, 2-fluorophenyl, 2-methoxyphenyl, 3-methoxyphenyl or 3-trifluoromethylphenyl.

Specifically preferred compounds of the present invention are compounds selected from the following:

6-fluoro-3-methyl-2-(4-phenyl-1-indolinyl)-quinoline-4-carboxylic acid, sodium salt, 6-fluoro-2-[4-(2-fluorophenyl)-1-indolinyl]-3-methylquinoline- 4-carboxylic acid, sodium salt, 6-fluoro-[4-(2-methoxyphenyl)-1-indolinyl]-3-methylquinoline-4-carboxylic acid, sodium salt, 6-fluoro-3-methyl-2-[4-(2-methylphenyl)-1-indolinyl]-quinoline- 4-carboxylic acid, sodium salt, 6-fluoro-[4-(3-methoxyphenyl)-1-indolinyl]-3-methylquinoline- 4-carboxylic acid, sodium salt, 6-fluoro-3-methyl-2-[4-(3-trifluoromethylphenyl)-1-indolinyl]-quinoline- 4-carboxylic acid, sodium salt, 6-fluoro-2-(4-phenyl-1-indolinyl)-quinoline-4-carboxylic acid, sodium salt, 6-fluoro-2-[4-(2-methylphenyl)-1-indolinyl]-quinoline-4-carboxylic acid, sodium salt, 6-fluoro-2-[4-(3-trifluoromethylphenyl)-1-indolinyl]-quinoline-4-carboxylic acid, sodium salt, 6-fluoro-3-methyl-2-(4-phenyl-1-indolyl)-quinoline-4-carboxylic acid, sodium salt, 6-fluoro-3-methyl-2-(4-phenyl-1-indolinyl)-quinoline-4-carboxylic acid, diethanolamine salt, 6-fluoro-3-methyl-2-(4-phenyl-1-indolinyl)-quinoline-4-carboxylic acid, N-methyl-D-glucamine salt, 6-fluoro-3-methyl-2-(4-phenyl-1-indolinyl)-quinoline-4-carboxylic acid, procaine salt, 6-fluoro-3-methyl-2-(4-phenyl-1-indolinyl)-quinoline-4-carboxylic acid, lysine salt, 6-fluoro-3-methyl-2-(4-phenyl-1-indolinyl)-quinoline-4-carboxylic acid, choline salt, 6-fluoro-3-methyl-2-(4-phenyl-1-indolinyl)-quinoline-4-carboxylic acid, tris-(hydroxymethyl) aminomethane salt, 6-fluoro-3-methyl-2-(5-phenyl-1-naphthyl)-quinoline-4-carboxylic acid, sodium salt, 6-fluoro-3-methyl-2-(7-phenyl-1-methyl-3-indolyl)-quinoline-4-carboxylic acid, sodium salt, 3-methyl-2-(7-phenyl-1-methyl-3-indolyl)-6-trifluoromethylquinoline-4-carboxylic acid, sodium salt.

6-fluoro-3-methyl-2-(6-fluoro-4-phenyl-1-benzimidazolyl)-quinoline-4-carboxylic acid

DETAILED DESCRIPTION OF THE INVENTION

In the present invention it has been discovered that the compounds of Formula I described herein are useful as immunosuppressive or immunomodulatory agents for the treatment and/or prevention in a mammal of organ transplantation rejection, graft versus host disease, and autoimmune diseases, including but not limited to systemic lupus erythematosus, rheumatoid arthritis, psoriasis, multiple sclerosis, and myasthenia gravis. The compounds of Formula I of the present invention are also useful for the treatment and/or prevention in a mammal of chronic inflammatory diseases, including but not limited to Crohn's disease, inflammatory bowel disease, rheumatoid arthritis, psoriasis, and primary biliary cirrhosis. The compounds of Formula I of the present invention are also useful for the treatment of tumors in a mammal, including leukemias and solid tumors, including tumors of the breast, colon, and lung.

The present invention also provides pharmaceutical compositions comprising a compound of Formula I and a pharmaceutically acceptable carrier.

Also provided in the present invention are methods of treatment and/or prevention of organ transplantation rejection, graft versus host disease, autoimmune diseases, or chronic inflammatory diseases comprising administering to a mammal in need of such treatment and/or prevention, a therapeutically effective amount of a compound of Formula I of the present invention.

The compounds of the present invention are also useful for the treatment of skin and muco-epithelial diseases in a mammal, such as psoriasis (in all its forms), lichen (including lichen planus), chronic eczema, icthyosis, pityriasis and chronic uticaria. Pharmaceutical compositions comprising a compound of Formula I formulated for topical administration are particularly useful for the treatment of such skin and muco-epithelial diseases.

The present invention also provides methods of treatment and/or prevention of immunological disorders including organ transplantation rejection, graft versus host disease, psoriasis, autoimmune diseases, and chronic inflammatory diseases in a mammal comprising administering to the mammal in a therapeutically effective amount for the treatment of a desired aforesaid disease a combination of: (i) a compound of Formula I as described below and (ii) at least one additional immunosuppressive agent. Such additional immunosuppressive agent may be selected from the group including but not limited to cyclosporin A (CSA or CsA) and analogs thereof, FK506 and analogs thereof, steroids, azathioprine (AZA), mycophenolic acid or the morpholine ethyl ester thereof, mycophenolate mofetil, rapamycin, 15-deoxyspergulin, mizorbine, leflunomide, OKT3, anti-interleukin-2 receptor antibodies, misoprostol, methotrexate, cyclophosphamide, and anti-lymphocyte/thymocyte serums.

The compounds of Formula I of the present invention may also be administered in combination with a non-steroidal anti-inflammatory agent, selected from the group including but not limited to, aspirin, ibuprofen, naproxen, indomethacin, diclofenac, sulindac, piroxicam, etodolac, ketoprofen, meclofenamate, suprofen, and tolmetin, for the treatment and/or prevention of organ transplantation rejection, graft versus host disease, psoriasis, autoimmune diseases, and chronic inflammatory diseases in a mammal.

There is also provided by this invention methods of treating cancer in a mammal, including leukemia and solid tumors, including pancreatic, mammary, colon, breast, lung, epithelial and melanoma tumors, comprising administering to a mammal bearing such a tumor a therapeutically effective tumor-inhibiting amount of a compound of Formula I as described above.

Compounds of Formula I of the present invention may also be administered in combination with other tumor inhibiting agents, including but not limited to, 5-fluorouracil, for the treatment of tumors in a mammal.

The compounds of Formula I of the present invention can be administered in combination with a second immunosuppressive agent, thereby to reduce the doses of each drug required to achieve the desired therapeutic effect. Thus, the combination treatment of the present invention permits the use of lower doses of each component, with reduced adverse, toxic effects of each component. A lower dosage minimizes the potential of side effects of the compounds, thereby providing an increased margin of safety relative to the margin of safety for each component when used as a single agent.

By "therapeutically effective amount" it is meant an amount of a compound of Formula I that when administered alone or in combination with a second additional immunosuppressive agent to a cell or mammal is effective to prevent or ameliorate the disease condition or the progression of the disease.

By "administered in combination" or "combination" when referring to component (i) and component (ii) of the present invention, it is meant that the components are administered concurrently to the cell or mammal being treated. When administered in combination each component may be administered at the same time or sequentially in any order at different points in time. Thus, component (i) and component (ii) may be administered separately but sufficiently closely in time so as to provide the desired therapeutic effect.

This invention also includes pharmaceutical kits comprising or consisting essentially of: a pharmaceutical composition comprising a compound of Formula I; or a compound of Formula I together with a pharmaceutical composition comprising at least one additional immunosuppressive agent. This invention also provides methods of using such pharmaceutical kits for the treatment of organ transplantation rejection, graft versus host disease, psoriasis and autoimmune diseases, including but not limited to rheumatoid arthritis, systemic lupus erythematosus, multiple sclerosis, myasthenia gravis as well as chronic inflammatory disease including but not limited to Crohn's disease and primary biliary cirrhosis, in a mammal.

This invention also includes combination products comprising pharmaceutical compositions comprising a compound of Formula I in physical combination or in a single dosage form with a second immunosuppressive agent, to pharmaceutical kits containing these combination products, and to methods of using these combination products for the treatment of organ transplantation rejection, graft versus host disease, psoriasis and autoimmune diseases, including but not limited to rheumatoid arthritis, systemic lupus erythematosus, multiple sclerosis, myasthenia gravis as well as chronic inflammatory disease including but not limited to Crohn's disease and primary biliary cirrhosis, in a mammal.

It will be recognized that certain of the compounds of Formula I may contain one or more asymmetric carbon atoms and may be isolated in optically active or racemic forms. All chiral, diastereomeric, and racemic forms are included in the present invention. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable occurs more than one time in any constituent or in Formula I or any other formula herein, its definition on each occurrence is independent of its definition at every other occurrence. Thus, for example, if a group is shown to be substituted with 0–2 $R^5$, then said group may optionally be substituted with up to two $R^5$ and $R^5$ at each occurrence is selected independently from the defined list of possible $R^5$. Also, combinations of substituents and/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge; "alkylthio" represents an alkyl group of indicated number of carbon atoms attached through a sulfur bridge; "alkylsulfinyl" represents an alkyl group of indicated number of carbon atoms attached through a sulfinyl bridge.

The term "substituted", as used herein, means that any one or more hydrogens on the designated atom is replaced with a selection from the indicated group, provided that the designated atom's normal valency is not exceeded, and that the substitution results in a stable compound.

By "stable compound" or "stable structure" is meant herein a compound that is sufficiently robust to survive isolation to a useful degree of purity from a reaction mixture, and formulation into an efficacious therapeutic agent.

As used herein, "pharmaceutically acceptable salts and prodrugs" refer to derivatives of the disclosed compounds that are modified by making acid or base salts, or by modifying functional groups present in the compounds in such a way that the modifications are cleaved, either in routine manipulation or in vivo, to the parent compounds. Examples include, but are not limited to, mineral or organic acid salts of basic residues such as amines; alkali or organic salts of acidic residues such as carboxylic acids; acetate, formate and benzoate derivatives of alcohols and amines; and the like. Salts of carboxylic acid residues may include, but are not limited to, sodium, potassium, diethanolamine, N-methyl-D-glucamine, procaine, lysine, choline or tris-(hydroxymethyl)aminomethane.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The disclosures of all of the references cited herein are hereby incorporated herein by reference in their entirety.

Synthesis

Compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

Compounds of Formula I, wherein A is

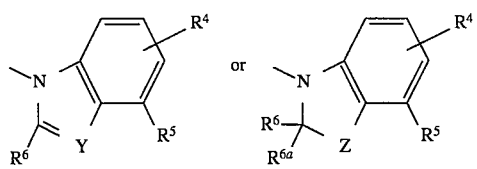

may be prepared from cinchoninic acids of Formula III

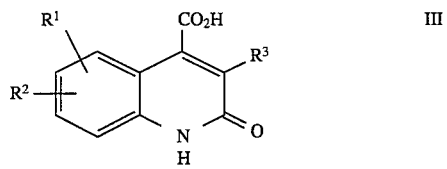

The cinchoninic acids of Formula III may be prepared using the same general procedure used to synthesize 2-hydroxycinchoninic acid (Jacobs et al., *Org. Syn. Coll. Vol.* 3, 456 (1955)). Compounds of Formula III are converted to compounds of Formula I by the series of reactions shown in Scheme 1 wherein the designation A is as defined above and the designations Y, Z, $R^1$, $R^2$, $R^3$, $R^4$, $R^5$, $R^6$, $R^{6A}$, $R^7$, $R^{7A}$, $R^8$, $R^9$, $R^{10}$ and $R^{11}$ are defined as provided in the Summary of the Invention in connection with formula (I).

Scheme 1

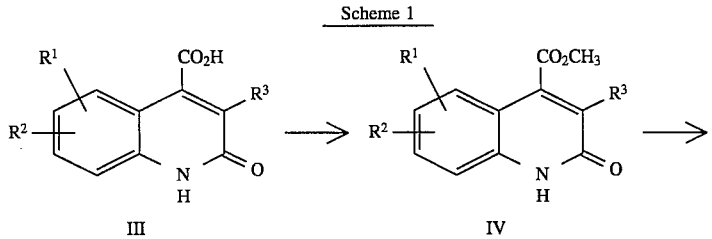

-continued
Scheme 1

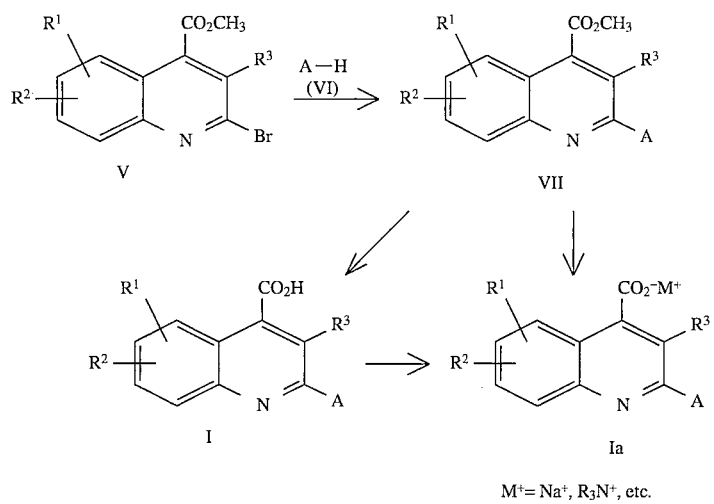

M⁺= Na⁺, R₃N⁺, etc.

Treatment of III with a base, for example, anhydrous potassium carbonate, in a suitable solvent, for example N,N-dimethylformamide, at room temperature, followed by treatment with an alkylating agent, for example, methyl iodide, gives rise to compounds of Formula IV. A compound of Formula IV may be treated with phosphorus oxybromide in toluene at reflux to provide a compound of Formula V. A compound of Formula V may be treated with a compound of Formula VI in the presence of a suitable solvent, for example absolute ethanol or 1-butanol, at reflux to provide a compound of Formula VII. Hydrolysis of ester VII to an acid of Formula I may be effected by methods known to one skilled in the art of organic synthesis. One such method is treatment with sodium hydroxide in refluxing aqueous ethanol, followed by treating the mixture, after allowing to cool to room temperature, with concentrated hydrochloric acid. The resulting acid of Formula I may be converted to its corresponding salt of Formula Ia by methods described above. When M is sodium, for example, conversion to the corresponding sodium salt Ia may be effected by treating I with one equivalent of sodium hydroxide in aqueous alcoholic solvent, for example ethanol, at reflux. Alternatively, VII may be converted directly to Ia by similarly treating VII with sodium hydroxide in aqueous alcoholic solvent, for example ethanol, at reflux.

Compounds of Formula I wherein A is a substituted 1-indolyl group, may alternately be prepared from a compound of Formula I, wherein A is a substituted 1-indolinyl group, by treatment with palladium on charcoal in an alcoholic solvent, for example absolute ethanol, at reflux in the presence of a hydrogen scavenger, for example cyclohexene as outlined in Scheme 2.

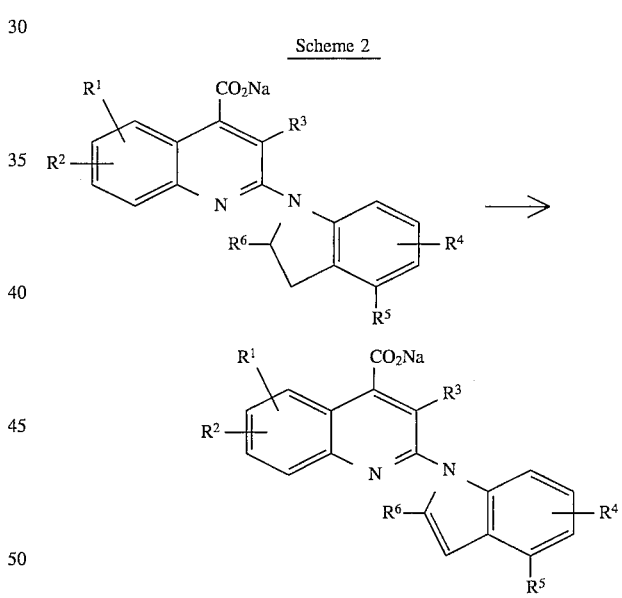

Scheme 2

Compounds of Formula VI, wherein A is a substituted 1-indolinyl moiety, may be prepared according to the reaction sequence depicted in Scheme 3.

Scheme 3

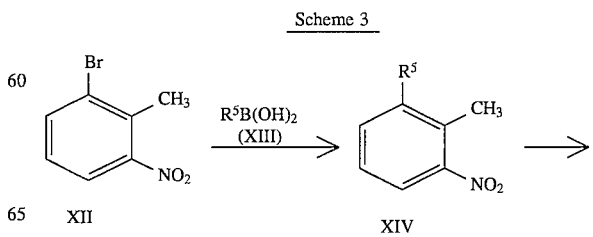

-continued
Scheme 3

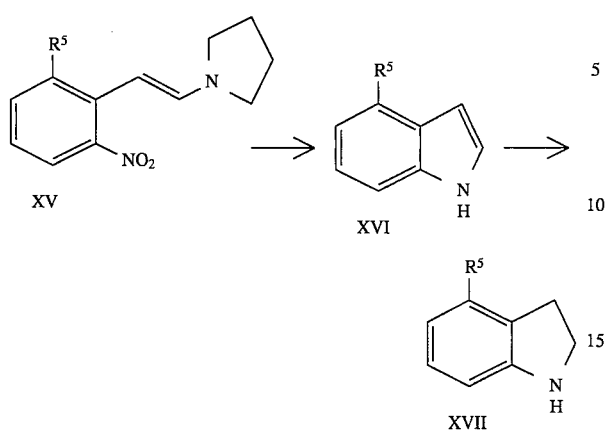

As an example, treatment of commercially available 2-bromo-6-nitrotoluene (XII) with a boronic acid, XIII, for example, phenylboronic acid, using a standard coupling reaction such as that described by Miyara et al. (Synth. Comm., 11, 513 (1981)), commonly referred to as a Suzuki coupling, provides compounds of Formula XIV. Treatment of XIV with N,N-dimethylformamide dimethyl acetal and pyrrolidine using conditions similar to those described by Batcho and Leimgruber (Org. Syn., 63, 214 (1985)) provides compounds of Formula XV. Subsequent treatment of XV with iron in glacial acetic acid and absolute ethanol, at reflux, provides compounds of Formula XVI. Reduction of XVI using sodium cyanoborohydride in glacial acetic acid, at or below room temperature, provides compounds of Formula XVII.

Compounds of Formula VI, wherein A is a substituted 1-benzimidazolyl moiety, may be prepared using the reaction sequence outlined in Scheme 4.

Scheme 4

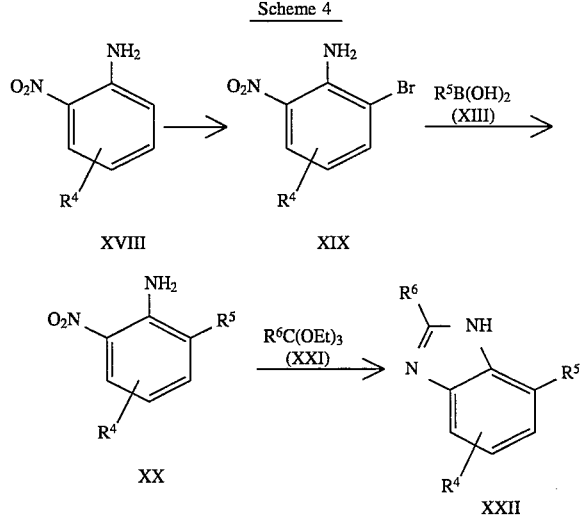

Thus, bromination of an appropriately substituted 2-nitroaniline XVIII, for example by treatment with pyridine in methylene chloride at −78° C., followed by dropwise addition of bromine provides compounds of Formula XIX. Suzuki reaction, similar to that described above for the conversion of XII to XIV, provides compounds of Formula XX. Reduction of XX, for example, by hydrogenation over palladium on charcoal as catalyst using absolute ethanol as solvent at room temperature, followed by treatment with an appropriately substituted orthoester XXI at reflux, provides compounds of Formula XXII.

Compounds of Formula I, wherein A is

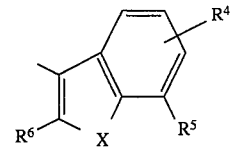

may be prepared from isatins of formula XXIII

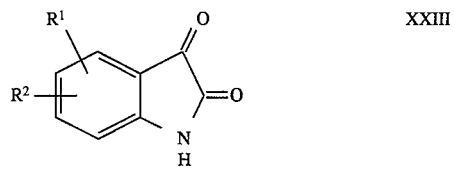

An appropriately substituted isatin of Formula XXIII is condensed with an appropriately substituted ketone XXIV as shown in Scheme 5.

Scheme 5

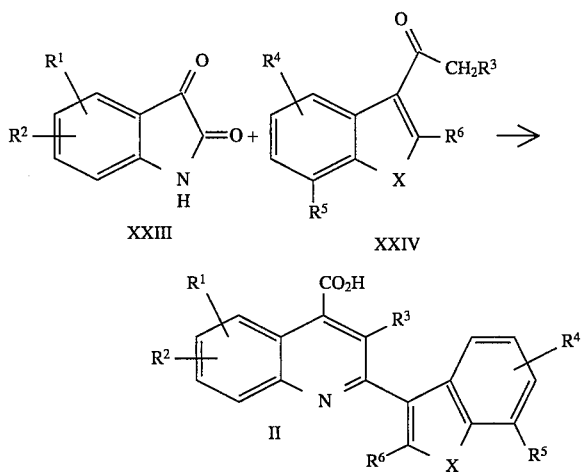

This condensation, commonly called the Pfitzinger condensation, is well known in the literature (for example, see Buu-Hoi et al., J. Org. Chem., 18 1209 (1953), and Jones, Quinolines Part I, 1977, Wiley, pp. 197–207). The reaction is usually carried out in a suitable solvent, such as absolute ethanol or a mixture of ethanol and water, in the presence of a suitable base, such as sodium hydroxide or potassium hydroxide, at a temperature in the range of about 5° C. to the boiling point of the solvent, preferably at the boiling point of the solvent. Acidification of the reaction mixture with a mineral acid such as hydrochloric acid or an organic acid such as acetic acid provides the compounds of Formula II. Alternatively, the compounds of Formula II may be directly isolated from the reaction mixture as a salt, such as the sodium or potassium salt.

An alternative procedure for the preparation of compounds of Formula I, wherein A is

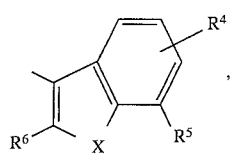

involves reaction of isatins XXIII with ketones XXIV under acidic conditions similar to those described by Lackey and Sternbach (*Synthesis*, 993 (1993)). Thus, a mixture of XXIII and XXIV in glacial acetic acid is heated to 75° C. for 5 minutes and concentrated hydrochloric acid is added. The mixture is heated to 105° C. for between 16 and 24 hours to afford the compounds of Formula II. Conversion to the sodium salt or potassium salt could be effected by treatment of compounds of Formula II with sodium hydroxide or potassium hydroxide, respectively, in refluxing absolute ethanol.

Isatins of Formula XXIII used as starting materials for preparation of compounds of Formula I are either commercially available or may be prepared using standard methods known to one skilled in the art as described by Papp and references given therein (*Adv. Heterocyclic Chem.*, 18, 1 (1975)).

Ketones of Formula XXIV, which may be used as starting materials to prepare compounds of Formula I, may be prepared using a variety of standard methods well known in the literature. Several applicable methods are herein described, but these methods are meant as illustrative examples only and do not constitute a limitation to the invention. Compounds of Formula XXIV, wherein X is $NR^7$, may be prepared as outlined in Scheme 6.

Scheme 6

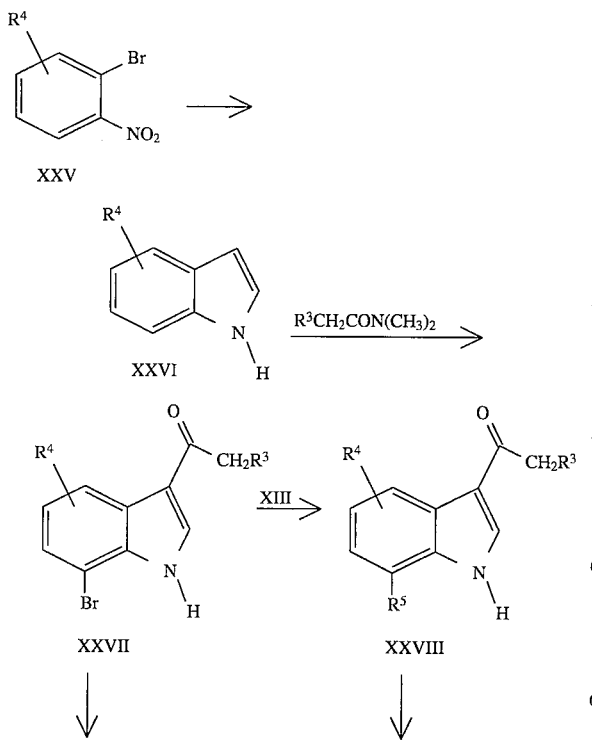

-continued
Scheme 6

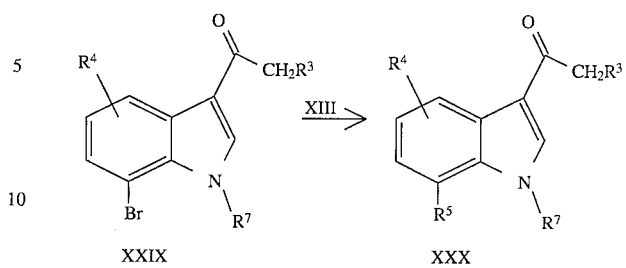

Thus, treatment of compounds of Formula XXV with three equivalents of vinylmagnesium bromide, using conditions similar to that described by Bartoli et al. (*Tetrahedron Lett.*, 30, 2129 (1989)), provides compounds of Formula XXVI. Reaction of XXVI with a N,N-dimethylalkanamide and phosphorus oxychloride, using a method similar to that described by Anthony (*J. Org. Chem.*, 25, 2049 (1960)), provides compounds of Formula XXVII. Suzuki coupling of XXVII with XIII, similar to that described above for conversion of XII to XIV, provides compounds of Formula XXVIII. Alkylation of XXVIII with a $C_1-C_3$ alkyl halide, for example $C_1-C_3$ alkyl iodide, in the presence of a suitable base, for example anhydrous potassium carbonate, in an appropriate solvent, for example N,N-dimethylformamide at room temperature, provides compounds of Formula XXX, wherein $R^7$ is $C_1-C_3$ alkyl. Alternatively, XXVII may be alkylated, similar to the conversion of XXVIII to XXX, to provide XXIX. Conversion of XXIX to XXX is carried out using conditions similar to those described for the transformation of XXVII to XXVIII by means of a Suzuki coupling.

Compounds of Formula XXIV, in which $R^4$ is H and X is CH=CH, may be prepared by the series of reactions outlined in Scheme 7.

Scheme 7

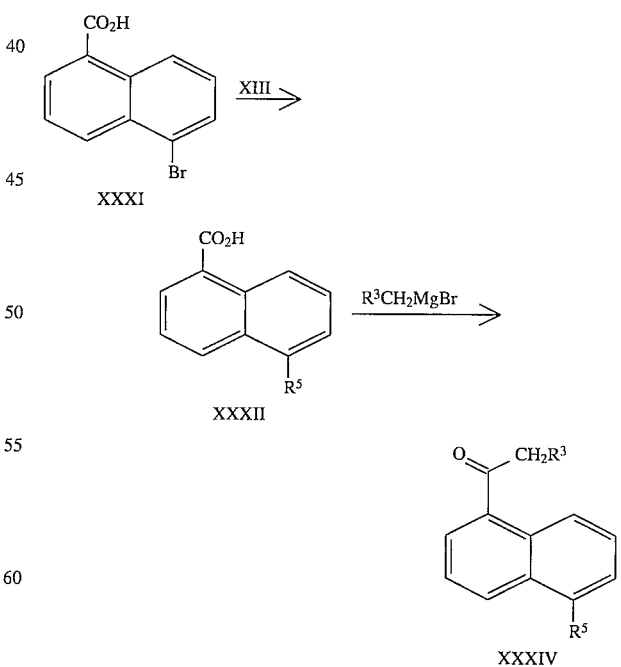

Thus, Suzuki coupling, similar to that described for the transformation of XII to XIV, involving 5-bromo-1-naphthoic acid XXXI (Short and Wang, *J. Chem. Soc.*, 991

(1950)) and a compound of Formula XIII provides compounds of Formula XXXII. Treatment of XXXII at low temperature, preferably at −70° C., in a suitable solvent, for example dry tetrahydrofuran, with one equivalent of a strong base, for example, methyllithium, followed by warming to room temperature and then treating with one equivalent of an alkylmagnesium bromide provides compounds of Formula XXXIV.

Compounds of Formula XXIV, in which X is oxygen and $R^4$ and $R^6$ are both H, may be synthesized by the sequence of steps depicted in Scheme 8.

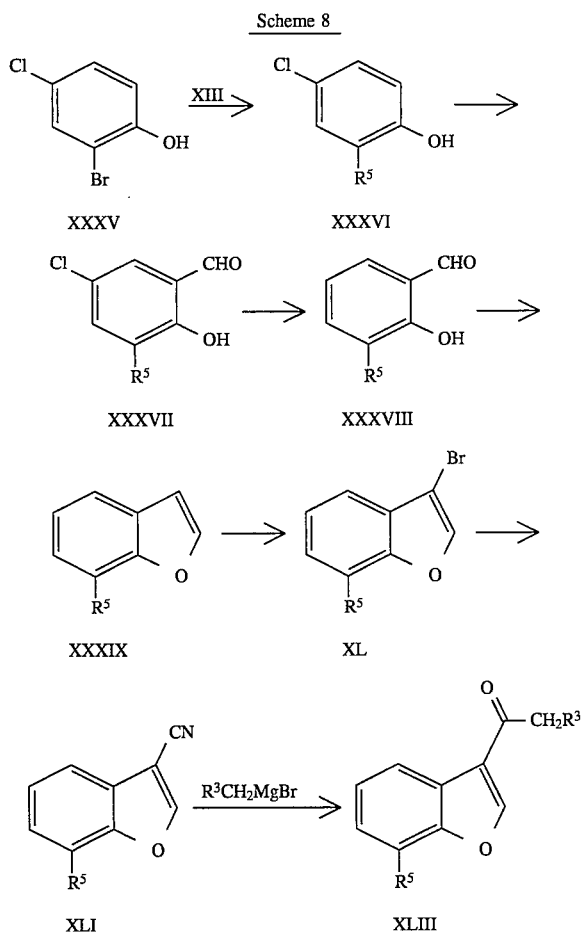

For example, Suzuki coupling of commercially available 2-bromo-4-chlorophenol (XXXV) with XIII, similar to that described for conversion of XII to XIV, could provide compounds of Formula XXXVI. Formylation followed by Fries rearrangement of XXXVI, similar to that described by March (*Advanced Organic Chemistry: Reactions, Mechanisms and Structure*, p. 428, McGraw-Hill, New York, 1968), could provide compounds of Formula XXXVII. Hydrogenolysis of XXXVII with triphenyltin hydride, similar to that described by Rothman and Becker (*J. Org. Chem.*, 24, 294 (1959)), could provide compounds of Formula XXXVIII. Treatment of XXXVIII with dimethylsulfoxonium methylide, using conditions similar to those described by Holt and Lowe (*Tetrahedron Lett.* (7), 683 (1966)), could provide compounds of Formula XXXIX. Bromination followed by dehydrobromination of XXXIX, similarly described by Kaiser and Zirkle in U.S. Pat. No. 3,010,971 issued Nov. 28, 1961, could lead to compounds of Formula XL. Subsequent addition of copper cyanide to XL, similar to that described by Kaiser and Zirkle (Ibid.), could yield XLI.

Treatment of XLI with an alkyl Grignard reagent, similar to that described by Kaiser and Zirkle (Ibid.), could provide starting ketone XLIII.

Compounds of Formula XXIV, in which X is sulfur and $R^4$ and $R^6$ both are H, may be prepared by the reactions shown in Scheme 9.

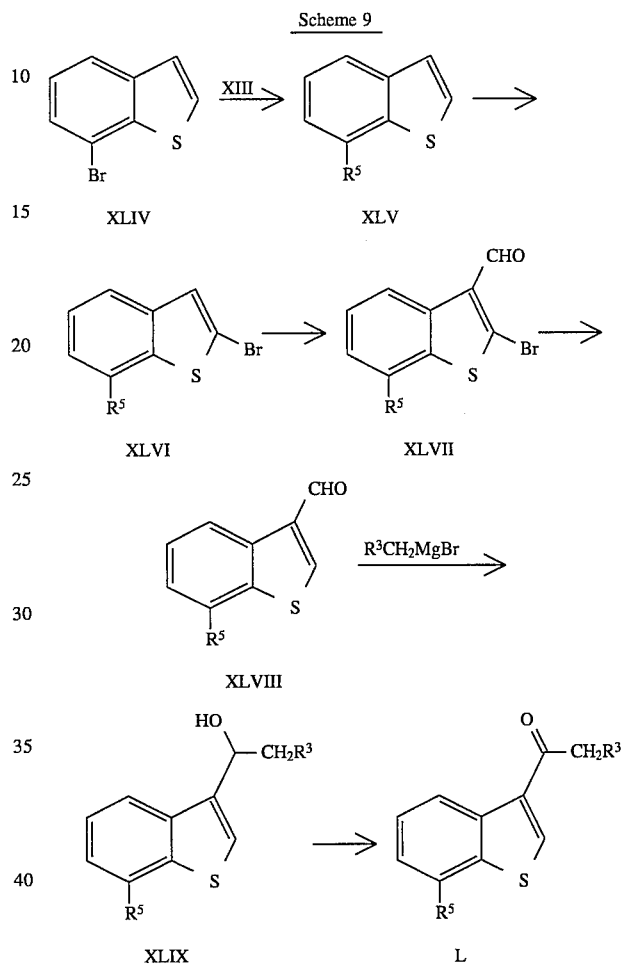

Thus, for example, Suzuki coupling of the known 7-bromothiophene (XLIV)(Faller, *Bull. Soc. Chim. Fr.* (11), 3667 (1966)) with XIII, similar to that described for the conversion of XII to XIV, could provide compounds of Formula XLV. Treatment of XLV with n-butyllithium followed by addition of bromine, analogous to that described by Shirley and Cameron (*J. Am. Chem. Soc.*, 74, 664 (1952)), could afford compounds of Formula XLVI. Formylation of XLVI by treatment with dichloromethyl butyl ether in methylene chloride in the presence of titanium tetrachloride followed by hydrolysis, as similarly described by Minh et al. (*Tetrahedron*, 28, 5393 (1972)), could provide compounds of Formula XLVII. Debromination of XLVII by addition of triphenyltin hydride, similar to that described by Rothman and Becker (*J. Org. Chem.*, 24, 294 (1959)), could afford compounds of Formula XLVIII. Addition of an alkyl Grignard reagent, using conditions similar to those outlined in March (*Advanced Organic Chemistry: Reactions, Mechanisms and Structure*, p. 684, McGraw-Hill, New York, 1968), could lead to production of an alcohol of Formula XLIX. Oxidation of XLIX, using standard methods known in the art for oxidation of secondary alcohols to ketones, for example, with pyridinium dichromate, similar to that described by Corey and Schmidt (*Tetrahedron Lett.* (5), 399 (1979)), could provide starting ketones of Formula L.

The compounds of this invention and their preparation can be further understood by the following procedures and examples, which exemplify but do not constitute a limit of their invention.

All melting points are uncorrected. All reactions were conducted under a nitrogen atmosphere except where otherwise noted. All commercial chemicals were used as received. Chromatography was performed with Merck silica gel 60 (230–400 mesh). The chromatography eluants are given as ratios by volume. Organic phases from solvent-solvent extractions were generally dried over magnesium sulfate, unless otherwise noted. Solvents were generally removed by evaporation under reduced pressure on a rotary evaporator unless otherwise noted. Peak positions for $^1$H NMR spectra are reported as parts per million (delta) downfield from the internal standard tetramethylsilane. Abbreviations for $^1$H NMR spectra are as follows: s=singlet, d=doublet, m=multiplet, dd=doublet of doublets, td=triplet of doublets, bs=broad singlet, bd=broad doublet, t=triplet, q=quartet. Infrared spectra are reported in reciprocal centimeters (cm$^{-1}$). Mass spectra were obtained using chemical ionization with ammonia as the reagent gas.

EXAMPLE 1

6-fluoro-3-methyl-2-(4-phenyl-1-indolinyl)quinoline-4-carboxylic acid

A. 5-fluoro-1-propionylisatin: A mixture of 5-fluoroisatin (350 g, 2.120 mol) in propionic anhydride (544 mL, 4.240 mol) was heated at reflux for 3 h. The solution was allowed to cool to room temperature and filtered. The resulting solid was triturated under diethyl ether and filtered to dryness to provide 5-fluoro-1-propionylisatin (374.7 g, 1.694 mol) as a brown solid in 80% yield, mp=150°–152° C.; NMR(CDCl$_3$): 8.45 (m, 1H), 7.42 (m, 2H), 3.12 (q, 2H), 1.28 (t, 3H).

B. 4-carboxy-6-fluoro-3-methylquinolin-2-one: To a mechanically stirred mixture of the compound of example 1A (350 g, 1.58 mol) and water (3L) was added sodium hydroxide pellets (126.6 g, 3.16 mol), and the mixture was heated at reflux for one hour. Heat was removed and activated charcoal (50 g) was added, and the mixture stirred 20 min. The mixture was then filtered through celite. Aqueous hydrochloric acid was added to the filtrate (6N, 264 mL, 1.58 mol). An orange precipitate was collected by filtration to provide the desired product (107.8 g, 0.489 mol) in 31% yield. mp>260° —C. NMR(d$_6$-DMSO): 7.26 (m, 3H), 1.98 (s, 3H).

C. 4-carbomethoxy-6-fluoro-3-methylquinolin-2-one: A mixture of the product of step 1B (100 g, 0.454 mol), anhydrous potassium carbonate (75 g, excess) and dry N,N-dimethylformamide (1L) was stirred at room temperature. To the resulting mixture was added iodomethane (60 mL, excess), and the mixture stirred for 16 h. The mixture was poured into saturated sodium bicarbonate (1L) and filtered. The resulting solid was washed with three 200 mL portions of water and air dried for 65 h. The desired product was obtained in 83% yield (88.7 g, 0.377 mol) as a white solid, mp=221°–223° C.; NMR (d$_6$-DMSO): 7.35–7.46 (m, 2H), 7.22 (d, 1H), 4.00 (s, 3H), 2.06 (s, 3H).

D. 2-bromo-4-carbomethoxy-6-fluoro-3-methylquinoline: A mixture of the product of step 1C (85 g, 0.361 mol), phosphorus oxybromide (184 g, excess) and toluene (1.5L) was heated at reflux for 2 h. The mixture was allowed to cool to room temperature and poured into water (1.5L). This mixture was extracted with three 1L portions of ethyl acetate. The combined organic layers were washed with brine, dried, filtered and solvent was removed from the filtrate to give the desired product in 92% yield (99.2 g, 0.332 mol) as an off-white solid, mp=157°–159° C.; NMR(d$_6$-DMSO): 8.08–8.14 (m, 1H), 7.77 (t, 1H), 7.60 (dd, 1H), 4.07 (s, 3H), 2.46 (s, 3H).

E. 2-nitro-6-phenyltoluene: A mixture of 2-bromo-6-nitrotoluene (28.86 g, 133.6 mmol), 2M Na$_2$CO$_3$ solution (135 mL), benzene (500 mL) and phenylboric acid (17.98 g, 147.4 mmol) was degassed by bubbling a stream of nitrogen through the solution for 30 min. To this was added tetrakis(triphenylphosphine)palladium (4.18 g, 3.6 mmol), and the mixture stirred at reflux for 16 h. The mixture was allowed to cool to room temperature and added to 200 mL water. The layers were separated and the aqueous layer was extracted with two 150 mL portions of ethyl acetate. The organic layers were combined, dried, filtered and solvent was removed from the filtrate. The residue was chromatographed (19:1 hexanes-ethyl acetate) to provide the desired product in 64.7% yield (18.45 g, 86.5 retool,) as a white powder, mp=68°–70° C.; NMR(CDCl$_3$): 7.22–7.81 (m, 8H), 2.36 (s, 3H); IR(KBr): 2932; Mass spectrum: m/z 231.1 (M+NH$_4$).

F. (E)-6-phenyl-2-nitro-β-pyrrolidinostyrene: A mixture of the product of step 1E (130 g, 10.00 mmol), N,N-dimethylformamide dimethyl acetal (1.388, 11.67 mmol), pyrrolidine (0.830 g, 11.67 mmol) and dry N,N-dimethylformamide (5 mL) was stirred at reflux for 2.5 h. The reaction was allowed to cool to room temperature and volatiles were removed. Added to the residue was methylene chloride (3 mL) and methanol (20 mL). Solvent was removed until a solid began to appear. The mixture was then cooled in an ice bath, and the solid was filtered. The filter cake was washed with chilled methanol (20 mL). The desired product was obtained in 84.9% yield (2. 500 g, 8.49 mmol, ) as a red solid, mp=134°–136° C.; NMR(CDCl$_3$): 7.01–7.55 (m, 8H), 6.20 (d, 1H), 4.97 (d, 1H), 2.98 (t, 4H), 1.80 (m, 4H); IR(KBr): 2858, 1622; Mass spectrum: m/z 295.0 (M+H).

G. 4-Phenylindole: A mixture of the product of step 1F (2.000 g, 6.794 mmol), iron (2.000 g, 35.810 mmol), glacial acetic acid (4.0 mL) and absolute ethanol (50 mL) was stirred at reflux for 2 h. The mixture was allowed to cool to room temperature, filtered, and the filtrate poured into 100 mL water. The mixture was extracted with three 75 mL portions of ethyl acetate, dried, filtered and solvent evaporated from the filtrate. The residue was chromatographed (5:1 hexanes-ethyl acetate) to provide the desired product (0.740 g, 3.829 mmol) as a white solid in 56.3% yield. mp=58°–60° C; NMR(CDCl$_3$): 8.23 (bs, 1H), 6.73–7.75 (m, 10H); IR(KBr): 3416, 3054, 1610; Mass spectrum: m/z 194.1 (M+H).

H. 4-phenylindoline: A mixture of the product of step 1G (1.95 g, 10.00 mmol) and glacial acetic acid (20 mL) was stirred at room temperature using a water bath to cool the solution. Added, portionwise over 15 min, was sodium cyanoborohydride (2.52 g, 40.10 mmol). After the addition was completed, the mixture was poured carefully into 200 mL saturated sodium bicarbonate solution and extracted with three 200 mL portions of diethyl ether. The combined organic layers were dried, filtered and solvent evaporated from the filtrate. The residue was chromatographed (4:1 hexanes-ethyl acetate) to provide the desired product (1.58 g, 8.09 mmol) in 80.9% yield as a white powder, mp=68°–70° C.; NMR(CDCl$_3$): 6.64–7.50 (m, 8H), 3.85 (bs, 1H), 3.56 (t, 2H), 3.10 (t, 2H); IR(KBr): 3380, 2850, 1594; Anal. Calcd. for C$_{14}$H$_{13}$N: C 86.12, H 6.71, N 7.17; Found C 85.92, H 6.80, N 7.13.

I. Methyl 6-fluoro-3-methyl-2-(4-phenyl-1-indolinyl)quinoline-4-carboxylate: A mixture of 2-bromo-4-carbomethoxy-6-fluoro-3-methylquinoline, obtained in step 1D, (5.96 g, 20.00 mmol), and the product of step 1H (3.90 g, 20.00 mmol) in absolute ethanol (100 mL) was stirred at reflux for 65 h. The mixture was allowed to cool to room temperature and the solid filtered to provide the desired product (6.64 g, 16.09 mmol) in 80.4% yield as a yellow solid, mp=213°–215° C.; NMR(CDCl$_3$): 6.52–7.93 (m, 11H), 4.18 (t, 2H), 4.10 (s, 3H), 3.23 (t, 2H), 2.45 (s, 3H); IR(KBr): 2860, 1728; Mass spectrum: m/z 413.1 (M+H).

J. 6-fluoro-3-methyl-2-(4-phenyl-1-indolinyl)quinoline-4-carboxylic acid: A mixture of the product of step 1I (0.512 g, 1.241 mmol), 50% aqueous ethanol (50 mL) and 50% aqueous sodium hydroxide (1.5 mL, (excess), w/w) was stirred at reflux for 16 h. The mixture was allowed to cool to room temperature and acidified with concentrated hydrochloric acid to pH 1. The resulting solid was filtered to dryness to provide the title compound (0.471 g, 1.182 mmol) in 95.2% yield as a yellow solid, mp=263°–265° C.; NMR(d$_6$-DMSO): 6.49–7.92 (m, 12H), 4.10(t, 2H), 3.21 (t, 2H), 2.40 (s, 3H); IR(KBr): 2862, 1706; Mass spectrum: m/z 399.0 (M+H).

EXAMPLE 2

6-fluoro-3-methyl-2-(4-phenyl-1-indolinyl)quinoline-4-carboxylic acid, sodium salt A mixture of the compound of Example 1I, (0.187 g, 0.453 mmol) 50% aqueous ethanol (50 mL) and 50% (w/w) aqueous sodium hydroxide (1 mL, excess) was stirred at reflux for 16 h. The mixture was filtered while hot and the filtrate added to 20 mL water. Added was 75 mL brine and the resulting solid suction dried. The filter cake was dissolved in 50 mL ethanol, filtered and solvent removed from the filtrate. The resulting solid was triturated under 2 mL water and filtered to dryness. The resulting solid was triturated under 5 mL dry acetone (dried over 4 Å molecular sieves) and filtered to dryness to provide the title compound (0.128 g, 0.304 mmol) as a yellow solid in 67.2% yield. mp=312°–314° C.; NMR(d$_6$-DMSO): 6.40–7.80 (m, 11H), 4.08 (t, 2H), 3.02 (t, 2H), 2.36 (s, 3H); IR(KBr): 3396, 2968; Mass spectrum: m/z 399.0 (M+H for free acid).

EXAMPLE 46

6-fluoro-3-methyl-2-(4-phenyl-1-indolyl)quinoline-4-carboxylic acid, sodium salt A mixture of the compound of Example 2 (2.400 g, 5.708 mmol) 10% palladium on charcoal (2.5 g) and cyclohexene (10 mL, excess) in absolute ethanol (100 mL), was stirred at reflux for 65 h. The mixture was allowed to cool to room temperature, filtered through celite and washed through with 100 mL absolute ethanol. Solvent was removed to provide the title compound (2.120 g, 5.066 mmol) in 88% yield as a yellow solid, mp=328°–330° C.(d); NMR(d$_6$-DMSO): 6.79–7.96 (m, 13H), 2.17 (s, 3H); IR(KBr): 3056, 1596; Mass spectrum: m/z 397.0 (M+H for free acid).

EXAMPLE 68

6-fluoro-3-methyl-2-(6-fluoro-4-phenyl-1-benzimidazolyl)quinoline-4-carboxylic acid A. 6-bromo-4-fluoro-2-nitroaniline: A mixture of 4-fluoro-2-nitroaniline (15.0 g, 96.08 mmol) and pyridine (7.7 mL, 96.08 mmol) in dichloromethane (75 mL) was cooled to −78° C. in a dry ice/acetone bath. A solution of bromine (4.95 mL 0 96.08 mmol) in dichloromethane (10 mL) was added dropwise. The resulting solution was stirred for 15 min at −78° C. and then at room temperature for 18 h. The mixture was poured into water and the layers were separated. The aqueous layer was extracted with two 50 mL portions of dichloromethane. The organic layers were combined, washed with water followed by brine, dried and solvent was evaporated. The residue was chromatographed (3:1 hexanes-ethyl acetate) to provide the desired product (11.41 g, 48.04 mmol) in 50% yield as a bright orange solid, mp=72°–74° C.; NMR(CDCl$_3$): 7.90 (dd, 1H), 7.57 (dd, 1H), 6.50 (bs, 2H); IR(KBr): 3488, 3376, 1514; Mass spectrum: m/z 233.9 (M+H).

B. 4-fluoro-6-nitro-2-phenylaniline: A stream of nitrogen was bubbled through a mixture of 2-bromo-4-fluoro-6-nitroaniline (7.5 g, 31.91 mmol), phenylboric acid (4.28 g, 35.10 mmol), 2.0M sodium carbonate solution (32 mL) and benzene (100 mL) for 30 min at room temperature. To this was added tetrakis(triphenylphosphine)palladium (1.11 g, 0.96 mmol) and the mixture was stirred at reflux for 18 h. The mixture was allowed to cool to room temperature, poured into 200 mL water and extracted with two 100 mL portions of ethyl acetate. The organic layers were combined, washed with brine, dried and solvent was removed. The residue was chromatographed (9:1 hexanes-ethyl acetate) to provide the desired product (6.47 g, 27.76 mmol) in 87% yield as an orange solid, mp=79°–80° C.; NMR(CDCl$_3$): 7.87 (dd, 1H), 7.44–7.56 (m, 3H), 7.40 (m, 2H), 7.14 (dd, 1H), 6.18 (bs, 2H); IR(KBr): 3486, 3338, 1520; Mass spectrum: m/z 233.1 (M+H).

C. 5-fluoro-7-phenylbenzimidazole: A mixture of the product of example 68B (5.0 g, 21.5 mmol), 10% (w/w) palladium on charcoal (500 mg, catalytic), and absolute ethanol (25 mL) was shaken under an atmosphere of hydrogen for one hour. The solution was filtered through celite and concentrated. The residue was dissolved in triethyl orthoformate (40 mL) and heated at reflux for one hour. The solution was allowed to cool to room temperature and filtered. The resulting solid was washed with chilled absolute ethanol to provide the desired product (3.58 g, 16.77 mmol) in 78% yield as a golden solid, mp=244°–245° C.; NMR(d$_6$-DMSO): 12.68 (bs, 1H), 8.30 (s, 1H), 7.93°–8.20 (bs, 2H), 7.51 (t, 2H), 7.36–7.48 (m, 2H), 7.28 (bd, 1H); IR(KBr): 3082, 2784, 1622; Mass spectrum: m/z 213.0 (M+H).

D. Methyl 6-fluoro-3-methyl-2-(6-fluoro-4-phenyl-1-benzimidazolyl)quinoline-4-carboxylate: A mixture of 2-bromo-4-carbomethoxy-6-fluoro-3-methylquinoline,obtained in Example 1D, (2.53 g, 8.48 mmol) and the product of example 68C (1.80 g, 8.48 mmol) in n-butanol (12 mL) was heated at reflux for 18 h. The reaction was allowed to cool to room temperature and solvent was removed. The residue was chromatographed (1:1 hexanes-ethyl acetate) to provide the desired product (0,135 g, 0.31 mmol) in 3.7% yield as a tan solid, mp=208–210° C.; NMR(CDCl$_3$): 8.27 (s, 1H), 8.13 (dd, 1H), 8.01 (d, 2H), 7.41–7.62 (m, 5H), 7.30 (dd, 1H), 7.06 (dd, 1H), 4.16 (s, 3H), 2.40 (s, 3H); IR(KBr): 1734; Mass spectrum: m/z 430.0 (M+H).

E. 6-fluoro-3-methyl-2-(4-phenyl-1-benzimidazolyl)quinoline-4-carboxylic acid, sodium salt: A mixture the compound of example 68D (0.122 g, 0.281 mmol) and absolute ethanol (3 mL) was heated to reflux. To this hot mixture was added 1.0 M aqueous sodium hydroxide (0.28 mL, 0,284 mmol). Heating was continued for 30 min until all solids dissolved. The reaction was allowed to cool to room temperature and poured into 5 mL water. The solution was extracted with two 5 mL portions of diethyl ether and then acidified with concentrated hydrochloric acid to pH 7.

Suction filtration provided the title compound (0,057 g, 0,134 mmol, 48%) as an off-white solid, mp=262°–264° C.; NMR($d_6$-DMSO): 8.82 (s, 1H), 0 8.15–8.24 (m, 3H), 7.84 (td, 1H), 7.65 (dd, 1H), 7.54 (t, 2H), 7.437.48 (m, 2H), 7.38 (dd, 1H), 2.39 (s, 3H); IR(KBr): 1716; Mass spectrum: m/z 416.10 (M+H).

EXAMPLE 70

6-fluoro-3-methyl-2-(7-phenyl-3-indolyl)quinoline-4-carboxylic acid

A. 7-bromo-3-propionylindole: A solution of N,N-dimethylpropionamide (8.0 mL, excess) was stirred at 5° C. To this cold solution was added phosphorus oxychloride (3.10 mL, 3.32 mmol) at such a rate so as to keep the temperature below 20° C. This was followed by slow addition of a solution of 7-bromoindole (4.30 g, 2.19 mmol) (7-bromoindole was prepared as described by Bartoli et al., *Tetrahedron Lett.*, 30 (16), 2129 (1989)) dissolved in N,N-dimethylpropionamide (4 mL), while keeping the temperature of the solution below 40° C. The cooling bath was removed and the mixture heated to 87° C. for 2 h. The mixture was allowed to cool to room temperature and poured into 200 mL water. The mixture was basified to pH 14 with 50% (w/w) aqueous sodium hydroxide and extracted with three 200 mL portions of diethyl ether. The combined organic layers were dried, filtered and solvent was removed from the filtrate. The residue was chromatographed (3:1 hexanes-ethyl acetate) to provide the desired product (3.59 g, 14.23 mmol) in 64% yield as a white solid, mp=148°–150° C.; NMR($CDCl_3$): 8.70 (bs, 1H), 7.15–8.18 (m, 4H), 2.94 (q, 2H), 1.25 (t, 3H); IR(KBr): 3256, 1644, 1616; Mass spectrum: m/z 251.9 (M+H for $^{79}$Br isotope).

B. 7-phenyl-3-propionylindole: A stream of nitrogen was passed through a mixture of the product of example 70A (3,230 g, 12.810 mmol), aqueous 2M sodium carbonate (13 mL), toluene (50 mL) and phenylboronic acid (1.724 g, 14.14 mmol) for 30 min. To the resulting mixture was added tetrakis(triphenylphosphine)palladium (0.500 g, catalytic), and the mixture was stirred at reflux for 4 h. The mixture was allowed to cool to room temperature and poured into 100 mL water. The mixture was extracted with three 100 mL portions of ethyl acetate, dried, filtered and solvent was removed from the filtrate. The residue was chromatographed (3:1 hexanes-ethyl acetate) to provide the desired product (2.801 g, 11.230 mmol) in 87.6% yield as a white solid, mp=145°–147° C.; NMR($CDCl_3$): 8.88 (bs, 1H), 7.25–8.43 (m, 9H), 2.94 (q, 2H), 1.25 (t, 3H); IR(KBr): 3306, 1634, 1600; Mass spectrum: m/z 250.0 (M+H).

C. 6-fluoro-3-methyl-2-(7-phenyl-3-indolyl)quinoline-4-carboxylic acid: A mixture of 5-fluoroisatin (0.545 g, 3.30 mmol) and glacial acetic acid (9 mL) was stirred at room temperature followed by addition of the compound of Example 70B (0,823 g, 3.30 mmol). The resulting mixture was placed in an oil bath pre-heated to 75° C. After stirring for 5 min, concentrated hydrochloric acid (3mL) was added, and the mixture heated to 105° C. for 24 h. The mixture was allowed to cool to room temperature and diluted with 15 mL water. The mixture was filtered and washed sequentially with 50 mL water, 9 mL absolute ethanol and 18 mL diethyl ether to provide the title compound (0.901 g, 2.27 mmol) in 68.8% yield as a tan solid, mp=340°–343° C.; NMR($d_6$-DMSO): 11.64 (bs, 1H), 7.20–8.22 (m, 13H), 2.62 (s, 3H); IR(KBr): 3144, 1734, 1608; Mass spectrum: m/z 397.0 (M+H).

EXAMPLE 71

6-fluoro-3-methyl-2-(7-phenyl-3-indolyl)quinoline-4-carboxylic acid, sodium salt A mixture of the compound of Example 70 (0.698 g, 1,760 mmol), 50% aqueous ethanol (40 mL) and 50% (w/w) aqueous sodium hydroxide (0.5 mL, excess) was heated to reflux. The mixture was then allowed to cool to room temperature and added to 300 mL brine. The mixture was filtered and the filtrate extracted with acetone. The top layer was separated and solvent removed. The residue was dissolved in absolute ethanol, filtered and solvent removed from the filtrate to provide the title compound (0.509 g, 1.216 mmol) in 69% yield as a light brown solid, mp=379–381° C.(d); NMR($d_6$-DMSO): 11.39 (bs, 1H), 7.18–8.15 (m, 12H), 2.50 (s, 3H); IR(KBr): 3450, 1586; Mass spectrum: m/z 397.0 (M+H for free acid).

EXAMPLE 74

6-fluoro-3-methyl-2-(1-methyl-7-phenyl-3-indolyl)quinoline-4-carboxylic acid

A. 1-methyl-7-phenyl-3-propionylindole: A mixture of the product obtained in Example 70B (1.20 g, 4.81 mmol), anhydrous potassium carbonate (1.00 g, excess) and dry N,N-dimethylformamide (6 mL) was stirred at room temperature. Added was 1.0 mL (excess) iodomethane and the mixture stirred for 16 h. The mixture was poured into 50 mL water and extracted with two 50 mL portions of ethyl acetate. The organic layers were combined, dried, filtered and solvent was removed from the filtrate. The resulting solid was recrystallized from hexanes to provide the desired product (0.79 g, 2.29 mmol) in 62% yield as a white solid, mp=107°–108° C.; NMR($CDCl_3$): 8.45 (d, 1H), 7.64 (s, 1H), 7.42 (s, 5H), 7.30 (t, 1H), 7.11 (d, 1H), 3.34 (s, 3H), 2.89 (q, 2H), 1.27 (t, 3H); IR(KBr): 1650; Mass spectrum: m/z 264.2 (M+H).

B. 6-fluoro-3-methyl-2-(1-methyl-7-phenyl-3-indolyl)quinoline-4-carboxylic acid: A mixture of 5-fluoroisatin (0.470 g, 2,850 mmol), the compound of Example 74A (0,750 g, 2.850 mmol) and glacial acetic acid (9 mL) was stirred at room temperature. The mixture was placed in an oil bath pre-heated to 75° C. and stirred 5 min. Added was 3 mL concentrated hydrochloric acid and the solution heated to 105° C. and stirred 16 h. The mixture was allowed to cool to room temperature and added was 15 mL water. The mixture was filtered and the filter cake washed sequentially with 50 mL water, 9 mL absolute ethanol and 18 mL diethyl ether. The title compound was obtained in 76.6% yield (0.897 g, 2.185 mmol), mp>285° C.; NMR($d_6$-DMSO): 8.24 (d, 1H), 8.14 (dd, 1H), 7.96 (s, 1H), 7.70 (td, 1H), 7.39–7.49 (m, 6H), 7.21 (t, 1H), 7.03 (d, 1H), 3.35 (s, 3H), 2.62 (s, 3H); IR(KBr): 1718, 1622; Mass spectrum: m/z 411 (M+H).

EXAMPLE 75

6-fluoro-3-methyl-2-(1-methyl-7-phenyl-indolyl)quinoline carboxylic acid, sodium salt A mixture of the compound of Example 74 (0.75 g, 1.83 mmol) and absolute ethanol (10 mL) was heated to reflux. To this was added aqueous 1N sodium hydroxide (1.83 mL, 1.83 mmol), and the mixture stirred one minute. The solution was allowed to cool to room temperature and filtered. Solvent was removed from the filtrate and added to the residue was 50 mL acetonitrile. Solvent was removed and the sample dried overnight on a vacuum pump to provide the title compound (0.698 g, 1.61 mmol) in 88% yield, mp=375°–8° C.(d); NMR($d_6$-DMSO): 8.17 (d, 1H), 7.93 (dd, 1H), 7.79 (s, 1H), 7.43–7.53 (m, 7H), 7.16 (t, 1H), 6.99 (d, 1H), 3.30 (s, 3H), 2.49 (s, 3H); IR(KBr): 3416, 1622, 1570; Mass spectrum: m/z 411.1 (M+H for free acid).

EXAMPLE 128

6-fluoro-3-methyl-2-(5-phenyl-1-naphthyl) quinoline-4-carboxylic acid, sodium salt A. 5-phenyl-1-naphthoic acid: A stream of nitrogen gas was bubbled through a mixture of 5-bromo-1-naphthoic acid (5.02 g, 20 mmol), (5-bromo-1-naphthoic acid was prepared by the method of Short and Wang, *J. Chem. Soc.*, 991 (1950)), phenylboric acid (2.93 g, 24 mmol), triethylamine (10 mL) and N,N-dimethylformamide (25 mL), with stirring at room temperature, for 30 min. To the resulting mixture was added tetrakis(triphenylphosphine)palladium (1.16 g, 1 mmol), and the mixture was heated at reflux for 20 h. The mixture was then allowed to cool to room temperature and poured into 150 mL of 1N aqueous hydrochloric acid and stirred for 20 min. The precipitate was collected by filtration, rinsed with water and dried. The solid was suspended in 50 mL water and treated with 20 mL of 1N aqueous sodium hydroxide. The resulting suspension was filtered, the filtrate acidified with 1N aqueous hydrochloric acid, the resulting solid filtered, washed with water and dried. Recrystallization from acetonitrile provided the desired product (1.88 g, 7.6 mmol) in 38% yield as white crystals, mp=218°–221° C.; NMR(CDCl$_3$): 9.12 (d, 1H), 8.40 (d, 1H), 8.17 (d, 1H), 7.73 (dd, 1 H), 7.5 (m, 7H); IR(KBr): 3060, 1700, 1678; Mass spectrum: m/z 249 (M+H).

B. 5-phenyl-1-propionylnaphthalene: A mixture of the compound of Example 128A (4.00 g, 16.1 mmol) and dry tetrahydrofuran (150 mL) was stirred at –70° C. and treated dropwise over 15 min with 1.4M methyllithium (in diethyl ether) (11.5 mL, 16.1 mmol). The resulting gray suspension was allowed to warm to room temperature over 1 h, when a clear solution resulted. A solution of 3.0M ethylmagnesium bromide (in diethyl ether, 5.4 mL, 16.1 mmol) was added over 2 min. The resulting mixture was stirred at room temperature for 48 h, then was poured into 150 mL of 1N aqueous hydrochloric acid. The layers were separated and the aqueous phase extracted with diethyl ether. The combined organic phases were dried and concentrated. The residue was chromatographed (toluene) to provide a yellowish oil which solidified upon standing. Recrystallization from absolute ethanol provided the desired product (1.52 g, 5.84 mmol) in 37% yield, mp=71°–73° C.; NMR(CDCl$_3$): 8.50 (d, 1H), 8.03 (d, 1H), 7.80 (d, 1H), 7.62 (dd, 1H), 7.45 (m, 7H), 3.09 (q, 2H), 1.30 (t, 3H); IR(KBr): 1686; Mass spectrum: m/z 261 (M+H).

C. 6-fluoro-3-methyl-2-(5-phenyl-1-naphthyl)quinoline-4-carboxylic acid, sodium salt: A mixture of the compound of Example 128B (0.780 g, 3.00 mmol), 5-fluoroisatin (0.495 g, 3.00 mmol) and absolute ethanol (10 mL) was treated with a solution of potassium hydroxide (1.68 g, 30 mmol) in water (5 mL) and heated to reflux. After 42 h the mixture was allowed to cool to room temperature, diluted with 40 mL water and the ethanol was removed. The aqueous residue was washed with diethyl ether, then acidified with concentrated aqueous hydrochloric acid. The resultant solid was collected by filtration, washed with water and dried to provide the free acid of the title compound (1.04 g, 2.55 mmol) in 85% yield as an off-white solid, mp>250° C.; NMR(d$_6$-DMSO): 8.15 (dd, 1H), 7.94 (d, 1H), 7.76 (td, 1H), 7.4–7.7 (m, 10H), 7.27 (d, 1H), 2.17 (s, 3H); IR(KBr): 2600–3600, 1718; Mass spectrum: m/z 408 (M+H). This solid was dissolved in 10 mL ethanol and 5 mL water, treated with 2.40 mL (2.40 mmol) of 1N aqueous sodium hydroxide and heated at reflux for 1 h. The mixture was allowed to cool to room temperature, filtered through celite, and the filtrate concentrated under vacuum. The residue was slurried in acetonitrile, filtered and the solid rinsed with acetonitrile and dried to provide the title compound (0.840 g, 1.95 mmol) in 82% yield as an off-white solid, mp>400° C.; NMR (d$_6$-DMSO): 7.8–8.0 (m, 2H), 7.4–7.7 (m, 11H), 7.28 (d, 1H), 2.04 (s, 3H).

The structures of compounds of Examples 1, 2, 46, 68, 70, 71, 74, 75 and 128 are listed in Tables 1–4. Using the above-described techniques or variations thereon appreciated by those skilled in the art of chemical synthesis, the additional compounds of Tables 1–4 (shown below) can also be prepared.

TABLE 1

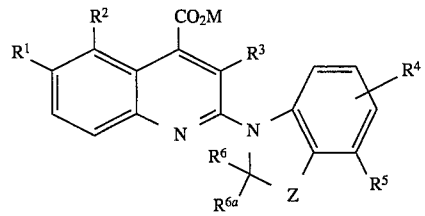

| Ex | M$^a$ | R$^1$ | R$^2$ | R$^3$ | R$^4$ | R$^5$ | R$^6$/R$^{6a}$ | Z | mp °C.$^b$ |
|---|---|---|---|---|---|---|---|---|---|
| 1 | H | F | H | CH$_3$ | H | phenyl | H/H | CH$_2$ | 263–5 |
| 2 | Na | F | H | CH$_3$ | H | phenyl | H/H | CH$_2$ | 312–4 |
| 3 | K | F | H | CH$_3$ | H | phenyl | H/H | CH$_2$ | 358–61(d) |
| 3a | Meg | F | H | CH$_3$ | H | phenyl | H/H | CH$_2$ | 152–4 |
| 3b | Pro | F | H | CH$_3$ | H | phenyl | H/H | CH$_2$ | 162–4 |
| 3c | Lys | F | H | CH$_3$ | H | phenyl | H/H | CH$_2$ | 231–4(d) |
| 3d | DEA | F | H | CH$_3$ | H | phenyl | H/H | CH$_2$ | 143–4 |
| 3e | Cho | F | H | CH$_3$ | H | phenyl | H/H | CH$_2$ | 202–3 |
| 3f | Tris | F | H | CH$_3$ | H | phenyl | H/H | CH$_2$ | 221–2(d) |
| 4 | Na | H | H | CH$_3$ | H | phenyl | H/H | CH$_2$ | 396–9 |
| 5 | Na | F | H | H | H | phenyl | H/H | CH$_2$ | 338–40(d) |
| 6 | Na | F | H | H | H | 3-trifluoromethyl phenyl | H/H | CH$_2$ | 306–8(d) |
| 7 | Na | F | H | H | H | 2-fluorophenyl | H/H | CH$_2$ | 357–9(d) |
| 8 | Na | F | H | H | H | 2-methylphenyl | H/H | CH$_2$ | 338–40(d) |
| 9 | Na | F | H | CH$_3$ | H | 2-methoxyphenyl | H/H | CH$_2$ | 283(d) |
| 10 | Na | F | H | CH$_3$ | H | 2-fluorophenyl | H/H | CH$_2$ | 295(d) |
| 11 | Na | F | H | CH$_3$ | H | 2-methylphenyl | H/H | CH$_2$ | 299–301 |
| 12 | Na | F | H | CH$_3$ | H | 3-trifluoromethyl phenyl | H/H | CH$_2$ | 294–5 |

TABLE 1-continued

| Ex | M[a] | R[1] | R[2] | R[3] | R[4] | R[5] | R[6]/R[6a] | Z | mp °C.[b] |
|---|---|---|---|---|---|---|---|---|---|
| 13 | Na | F | H | $CH_3$ | H | 3-methoxyphenyl | H/H | $CH_2$ | 309 |
| 14 | Na | F | H | $CH_3$ | H | 2-trifluoromethoxyphenyl | H/H | $CH_2$ | |
| 15 | Na | F | H | $CH_3$ | H | 2-chlorophenyl | H/H | $CH_2$ | |
| 16 | Na | F | H | $CH_3$ | H | 2-thiomethylphenyl | H/H | $CH_2$ | |
| 17 | Na | F | H | $CH_3$ | H | 2-(trifluoromethylthio)phenyl | H/H | $CH_2$ | |
| 18 | Na | F | H | $CH_3$ | H | 2-dimethylaminophenyl | H/H | $CH_2$ | |
| 19 | Na | F | H | $CH_3$ | H | 3-chlorophenyl | H/H | $CH_2$ | |
| 20 | Na | F | H | $CH_3$ | H | 3-fluorophenyl | H/H | $CH_2$ | |
| 21 | Na | F | H | $CH_3$ | H | 3-methylphenyl | H/H | $CH_2$ | |
| 22 | Na | F | H | $CH_3$ | H | 3-trifluoromethoxyphenyl | H/H | $CH_2$ | |
| 23 | Na | F | H | $CH_3$ | H | 3-methylthiophenyl | H/H | $CH_2$ | |
| 24 | Na | F | H | $CH_3$ | H | 3-(trifluoromethylthio)phenyl | H/H | $CH_2$ | |
| 25 | Na | F | H | $CH_3$ | H | 3-dimethylaminophenyl | H/H | $CH_2$ | |
| 26 | Na | F | Cl | $CH_3$ | H | Phenyl | H/H | $CH_2$ | |
| 27 | Na | $CF_3$ | H | $CH_3$ | H | Phenyl | H/H | $CH_2$ | |
| 28 | Na | F | H | CN | H | Phenyl | H/H | $CH_2$ | |
| 29 | Na | F | H | $N(CH_3)_2$ | H | Phenyl | H/H | $CH_2$ | |
| 30 | Na | F | H | $OCH_3$ | H | Phenyl | H/H | $CH_2$ | |
| 31 | Na | F | H | $SCH_3$ | H | Phenyl | H/H | $CH_2$ | |
| 32 | Na | F | H | $NO_2$ | H | Phenyl | H/H | $CH_2$ | |
| 33 | Na | F | H | $CF_3$ | H | Phenyl | H/H | $CH_2$ | |
| 34 | Na | F | H | $SCF_3$ | H | Phenyl | H/H | $CH_2$ | |
| 35 | Na | F | H | $CH_3$ | 6-F | Phenyl | H/H | $CH_2$ | >250 |
| 36 | Na | F | H | $CH_3$ | 6-$N(CH_3)_2$ | Phenyl | H/H | $CH_2$ | |
| 37 | Na | F | H | $CH_3$ | 6-$OCH_3$ | Phenyl | H/H | $CH_2$ | >250 |
| 38 | Na | F | H | $CH_3$ | 6-$CH_3$ | Phenyl | H/H | $CH_2$ | |
| 39 | Na | F | H | $CH_3$ | H | Phenyl | H/$CH_3$ | $CH_2$ | |
| 40 | Na | F | H | $CH_3$ | H | Phenyl | $CH_3$/$CH_3$ | $CH_2$ | |
| 41 | Na | F | H | $CH_3$ | H | 2-thienyl | H/H | $CH_2$ | |
| 42 | Na | F | H | $CH_3$ | H | 2-furyl | H/H | $CH_2$ | |
| 43 | Na | F | H | $CH_3$ | H | 2-thiazolyl | H/H | $CH_2$ | |
| 44 | Na | F | H | $CH_3$ | H | 2-oxazolyl | H/H | $CH_2$ | |
| 45 | Na | F | H | $CH_3$ | H | phenyl | H/H | $C(CH_3)_2$ | |

[a]Meg = N-methyl-D-glucamine salt; Pro = procaine salt; Lys = lysine salt; DEA = diethanolamine salt; Cho = choline salt; Tris = tris(hydroxymethyl)aminomethane salt.
[b](d) indicates decomposition occurred at the temperature or range shown.

TABLE 2

| Ex. No. | M | R[4] | R[5] | Y | mp °C. |
|---|---|---|---|---|---|
| 46 | H | H | phenyl | CH | 310-2(d) |
| 47 | Na | H | phenyl | CH | 328-30(d) |
| 48 | Na | H | 2-chlorophenyl | CH | |
| 49 | Na | H | 2-fluorophenyl | CH | |
| 50 | Na | H | 2-methylphenyl | CH | |
| 51 | Na | H | 2-methoxyphenyl | CH | |
| 52 | Na | H | 2-trifluoromethylphenyl | CH | |
| 53 | Na | H | 2-trifluoromethoxyphenyl | CH | |
| 54 | Na | H | 2-(methylthio)phenyl | CH | |

TABLE 2-continued

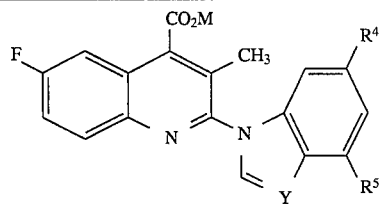

| Ex. No. | M | R⁴ | R⁵ | Y | mp °C. |
|---|---|---|---|---|---|
| 55 | Na | H | 2-(trifluoromethylthio)phenyl | CH | |
| 56 | Na | H | 2-dimethylaminophenyl | CH | |
| 57 | Na | H | 3-chlorophenyl | CH | |
| 58 | Na | H | 3-fluorophenyl | CH | |
| 59 | Na | H | 3-methylphenyl | CH | |
| 60 | Na | H | 3-methoxyphenyl | CH | |
| 61 | Na | H | 3-trifluoromethylphenyl | CH | |
| 62 | Na | H | 3-trifluoromethoxyphenyl | CH | |
| 63 | Na | H | 3-(methylthio)phenyl | CH | |
| 64 | Na | H | 3-(trifluoromethylthio)phenyl | CH | |
| 65 | Na | H | 3-dimethylaminophenyl | CH | |
| 66 | Na | H | phenyl | CCH₃ | |
| 67 | Na | H | phenyl | N | |
| 68 | H | F | phenyl | N | 262–4 |
| 69 | Na | F | phenyl | N | |

TABLE 3

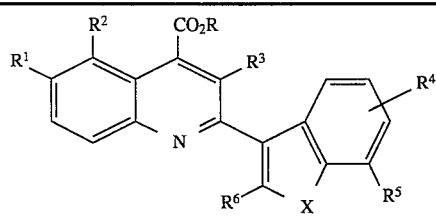

| Ex | R | R¹ | R² | R³ | R⁴ | R⁵ | R⁶ | X | mp °C.ᵃ |
|---|---|---|---|---|---|---|---|---|---|
| 70 | H | F | H | CH₃ | H | phenyl | H | NH | 340–3(d) |
| 71 | Na | F | H | CH₃ | H | phenyl | H | NH | 379–81(d) |
| 72 | H | CF₃ | H | CH₃ | H | phenyl | H | NCH₃ | >265 |
| 73 | Na | CF₃ | H | CH₃ | H | phenyl | H | NCH₃ | >265 |
| 74 | H | F | H | CH₃ | H | phenyl | H | NCH₃ | >285 |
| 75 | Na | F | H | CH₃ | H | phenyl | H | NCH₃ | 375–8(d) |
| 76 | H | F | H | CH₃ | H | 2-methoxyphenyl | H | NCH₃ | 313–5(d) |
| 77 | Na | F | H | CH₃ | H | 2-methoxyphenyl | H | NCH₃ | >285 |
| 78 | Na | F | H | CH₃ | H | 2-chlorophenyl | H | NCH₃ | |
| 79 | Na | F | H | CH₃ | H | 2-fluorophenyl | H | NCH₃ | |
| 80 | Na | F | H | CH₃ | H | 2-methylphenyl | H | NCH₃ | |
| 81 | Na | F | H | CH₃ | H | 2-trifluoromethylphenyl | H | NCH₃ | |
| 82 | Na | F | H | CH₃ | H | 2-trifluoromethoxyphenyl | H | NCH₃ | |
| 83 | Na | F | H | CH₃ | H | 2-(methylthio)phenyl | H | NCH₃ | |
| 84 | Na | F | H | CH₃ | H | 2-(trifluoromethylthio)phenyl | H | NCH₃ | |
| 85 | Na | F | H | CH₃ | H | 2-dimethylaminophenyl | H | NCH₃ | |
| 86 | Na | F | H | CH₃ | H | 3-methoxyphenyl | H | NCH₃ | |
| 87 | Na | F | H | CH₃ | H | 3-chlorophenyl | H | NCH₃ | |
| 88 | Na | F | H | CH₃ | H | 3-fluorophenyl | H | NCH₃ | |
| 89 | Na | F | H | CH₃ | H | 3-methylphenyl | H | NCH₃ | |
| 90 | Na | F | H | CH₃ | H | 3-trifluoromethylphenyl | H | NCH₃ | |
| 91 | Na | F | H | CH₃ | H | 3-trifluoromethoxyphenyl | H | NCH₃ | |
| 92 | Na | F | H | CH₃ | H | 3-(methylthio)phenyl | H | NCH₃ | |
| 93 | Na | F | H | CH₃ | H | 3-(trifluoromethylthio)phenyl | H | NCH₃ | |
| 94 | Na | F | H | CH₃ | H | 3-dimethylaminophenyl | H | NCH₃ | |
| 95 | Na | F | H | CH₃ | H | 2-thienyl | H | NCH₃ | |
| 96 | H | F | H | CH₃ | H | 3-furyl | H | NCH₃ | 301–2(d) |
| 97 | Na | F | H | CH₃ | H | 2-thiazolyl | H | NCH₃ | |
| 98 | H | F | H | CH₃ | H | 2-oxazolyl | H | NCH₃ | |

TABLE 3-continued

| Ex | R | R$^1$ | R$^2$ | R$^3$ | R$^4$ | R$^5$ | R$^6$ | X | mp °C.$^a$ |
|---|---|---|---|---|---|---|---|---|---|
| 99  | Na | F | H | CH$_3$ | 4-Cl        | phenyl | H | NCH$_3$ | |
| 100 | Na | F | H | CH$_3$ | 4-F         | phenyl | H | NCH$_3$ | |
| 101 | Na | F | H | CH$_3$ | 4-CH$_3$    | phenyl | H | NCH$_3$ | |
| 102 | Na | F | H | CH$_3$ | 4-OCH$_3$   | phenyl | H | NCH$_3$ | |
| 103 | Na | F | H | CH$_3$ | 4-CF$_3$    | phenyl | H | NCH$_3$ | |
| 104 | Na | F | H | CH$_3$ | 4-OCF$_3$   | phenyl | H | NCH$_3$ | |
| 105 | Na | F | H | CH$_3$ | 4-SCH$_3$   | phenyl | H | NCH$_3$ | |
| 106 | Na | F | H | CH$_3$ | 4-SCF$_3$   | phenyl | H | NCH$_3$ | |
| 107 | Na | F | H | CH$_3$ | 4-N(CH$_3$)$_2$ | phenyl | H | NCH$_3$ | |
| 108 | Na | F | H | CH$_3$ | 5-Cl        | phenyl | H | NCH$_3$ | |
| 109 | Na | F | H | CH$_3$ | 5-F         | phenyl | H | NCH$_3$ | |
| 110 | Na | F | H | CH$_3$ | 5-CH$_3$    | phenyl | H | NCH$_3$ | |
| 111 | Na | F | H | CH$_3$ | 5-OCH$_3$   | phenyl | H | NCH$_3$ | |
| 112 | Na | F | H | CH$_3$ | 5-CF$_3$    | phenyl | H | NCH$_3$ | |
| 113 | Na | F | H | CH$_3$ | 5-OCF$_3$   | phenyl | H | NCH$_3$ | |
| 115 | Na | F | H | CH$_3$ | 5-SCH$_3$   | phenyl | H | NCH$_3$ | |
| 115 | Na | F | H | CH$_3$ | 5-SCF$_3$   | phenyl | H | NCH$_3$ | |
| 116 | Na | F | H | CH$_3$ | 5-N(CH$_3$)$_2$ | phenyl | H | NCH$_3$ | |
| 117 | Na | F | H | CH$_3$ | 6-Cl        | phenyl | H | NCH$_3$ | |
| 118 | Na | F | H | CH$_3$ | 6-F         | phenyl | H | NCH$_3$ | |
| 119 | Na | F | H | CH$_3$ | 6-CH$_3$    | phenyl | H | NCH$_3$ | |
| 120 | Na | F | H | CH$_3$ | 6-OCH$_3$   | phenyl | H | NCH$_3$ | |
| 121 | Na | F | H | CH$_3$ | 6-CF$_3$    | phenyl | H | NCH$_3$ | |
| 122 | Na | F | H | CH$_3$ | 6-OCF$_3$   | phenyl | H | NCH$_3$ | |
| 123 | Na | F | H | CH$_3$ | 6-SCH$_3$   | phenyl | H | NCH$_3$ | |
| 124 | Na | F | H | CH$_3$ | 6-SCF$_3$   | phenyl | H | NCH$_3$ | |
| 125 | Na | F | H | CH$_3$ | 6-N(CH$_3$)$_2$ | phenyl | H | NCH$_3$ | |
| 126 | Na | F | H | CH$_3$ | H           | phenyl | H | O | |
| 129 | Na | F | H | CH$_3$ | H           | phenyl | H | S | |
| 130 | H  | F | H | H      | H           | phenyl | H | S | |
| 131 | H  | F | H | CH$_3$ | H           | phenyl | CH$_3$ | S | |
| 132 | H  | F | Cl | CH$_3$ | H           | phenyl | CH$_3$ | S | |
| 133 | H  | F | H | SCH$_3$ | H          | phenyl | H | NCH$_3$ | |

TABLE 4

| Ex | M | R$^1$ | R$^2$ | R$^3$ | R$^4$ | R$^5$ | mp °C. |
|---|---|---|---|---|---|---|---|
| 127 | H  | F | H | CH$_3$ | H | phenyl | >250 |
| 128 | Na | F | H | CH$_3$ | H | phenyl | >400 |

Utility

The compounds of Formula I suppress or inhibit an in vitro immune response (i.e. have potent immunosuppressive activity) and are therefore useful as immunosuppressants for the treatment and/or prevention of organ transplantation rejection, graft versus host disease, autoimmune diseases and chronic inflammatory diseases. The ability of the compounds of the present invention to suppress or inhibit an immune cell reaction is demonstrated using the human mixed lymphocyte reaction test described below. The compounds of the present invention inhibit contact sensitivity response as demonstrated, for example, using the contact sensitivity model described below. The ability of the compounds of the present invention to exhibit antiinflammatory and antiproliferative effects in vivo may be demonstrated using the animal models described below. The anticancer activity of the compounds of the present invention may be demonstrated, for example, using the in vitro and in vivo models described below.

The human mixed lymphocyte reaction described below is used for the determination of transplantation compatibility between the donor (graft) and the recipient (Park and Good, p. 71, in *Tissue Typing and Organ Transplantation* (Yunis et al.), 1973, Academic Press Inc., NY). The human mixed lymphocyte reaction is an in vitro immune response. Inhibition of the human mixed lymphocyte reaction immune response is a standard assay used in the field of immunology, which is considered to be indicative of in vivo immunosuppressive activity. In particular, activity in the mixed lymphocyte reaction indicates that the compounds of the present invention should be effective in the treatment and/or prevention of organ transplantation rejection and graft versus host disease. The human mixed lymphocyte is also used as a model system for immune reactions involving T-cell-mediated immune responses. Such T-cell-mediated immune responses have been linked to the disease pathology associated with autoimmune diseases, chronic inflammatory diseases, graft versus host disease and organ transplantation rejection.

Thus, in view of the results presented below, the compounds of Formula I of the present invention are expected to be efficacious in psoriasis, rheumatoid arthritis, autoimmune diseases, and chronic inflammatory diseases, all of which involve T-lymphocyte immune responses. Also, the antiproliferative activity displayed by the compounds of the present invention indicates the utility of these compounds for the inhibition of tumor growth.

Contact sensitivity to 2,4-dinitrofluorobenzene (DNFB) has been extensively studied and characterized in the mouse to determine the regulatory mechanisms involved in cell mediated immune responses (Claman et al., *Immunol. Rev.* 50:105, 1980; Young and Young, "Cutaneous Models of Inflammation for the Evaluation of Topical and Systemic Pharmacological Agents" in *Pharmacological Methods in the Control of Inflammation* (Chang and Lewis, Eds.), Alan R. Liss, Inc., New York, pp. 215–231, 1989). This is an antigen-specific T-cell mediated inflammatory response that represents delayed-type hypersensitivity reactions seen in both humans and other mammals. This contact sensitivity animal model is used routinely in many laboratories for pharmacological screening of antiinflammatory agents.

Contact sensitivity to DNFB is a form of delayed-type hypersensitivity which has been extensively studied to gain an understanding of the regulation of immunologic processes (Claman et al., supra). This reaction is mediated by T-lymphocytes that become sensitized to antigen by proliferating and developing into mature effector cells (Claman et al., supra). This cell-mediated immune response (T-cell mediated immunity) is central to many disease states such as organ transplantation rejection and graft versus host disease (Benacerraf and Unanue (1979), *Textbook of Immunology*, Williams and Wilkins Co.; Eisen (1980), *Immunolgy, An Introduction to Molecular and Cellular Principles of the Immune Responses*, Harper and Row, Inc.; Loveland and McKenzie (1982), *Immunology*, 46:313–320; Gallin et al. (1988), *Inflammation, Basic Principles and Clinical Correlates*, Raven Press).

The contact sensitivity model used for this study is an extensively used model system for delayed-type hypersensitivity reactions involving cell-mediated immune responses (T-cell mediated responses), which have been linked to the disease pathology associated with organ transplantation rejection, graft versus host disease, multiple sclerosis, myasthenia gravis, systemic lupus erythematosus, rheumatoid arthritis, and other chronic inflammatory diseases and autoimmune diseases for which the T-cell is pivotal to mounting an immune or autoimmune response.

The present results show that the compounds of the present invention have both immunomodulating and anti-inflammatory effectiveness. Based on these results, the compounds of the present invention are expected to be efficacious in treating and/or preventing organ transplantation rejection, graft versus host disease, and other autoimmune diseases and chronic inflammatory diseases, such as those described above, in humans and other mammals.

Human Mixed Lymphocyte Reaction Test (MLR)

Blood was obtained by venipuncture from two non-related human donors. Peripheral blood mononuclear cells (PBMC) were isolated from these samples by using the Leuco Prep procedure (Becton-Dickinson). PBMC were washed twice in phosphate buffered saline (without calcium and magnesium) and the separate cell isolations were adjusted to the appropriate concentrations in media (RPMI 1640) supplemented with 10% human AB serum and 50 uL/mL gentamicin. Cells from donor A ($2 \times 10^5$) were incubated with cells from donor B ($2 \times 10^5$) with or without compound in 96 well round bottom microtiter plates at 37° C., 5% $CO_2$ for 6 days. Eighteen hours prior to harvesting cells from the plates, all wells were pulsed with 1 uCi of tritiated-thymidine. Cells from the plates were washed on day 6 and tritiated-thymidine incorporation was determined using a scintillation counter.

MLR test results for representative compounds of the present invention are shown in Table A. In this table, ++ indicates an $IC_{50}$ value less than $5 \times 10-8$ M, and + indicates an $IC_{50}$ value in the range $5 \times 10-8$ M to $1 \times 10-5$ M.

TABLE A

| Compound | $IC_{50}$ |
| --- | --- |
| cyclosporin | ++ |
| methotrexate | ++ |
| Ex. 1 | ++ |
| Ex. 2 | ++ |
| Ex. 4 | + |
| Ex. 5 | ++ |
| Ex. 6 | ++ |
| Ex. 7 | ++ |
| Ex. 8 | ++ |
| Ex. 9 | ++ |
| Ex. 10 | ++ |
| Ex. 11 | ++ |
| Ex. 12 | ++ |
| Ex. 13 | ++ |
| Ex. 46 | + |
| Ex. 47 | + |
| Ex. 68 | + |
| Ex. 73 | ++ |
| Ex. 75 | + |
| Ex. 128 | + |

Assay of Contact Sensitivity Response to DNFB in Mice

Balb/c female mice (approximately 20 g, Charles River) were sensitized on the shaved abdomen with 25 uL of 0.5% 2,4-dinitrofluorobenzene (DNFB) (Eastman Kodak Co.) in a vehicle of 4:1 acetone: olive oil on days 0 and 1. Mice were ear challenged with 20 uL of 0.2% DNFB in a vehicle of 4:1 acetone: olive oil on day 5. An identical segment of the ear was measured immediately before challenge and 24 hours later with an engineer's micrometer. Ear swelling was expressed as the difference in ear thickness before and after challenge in units of 10–4 inches±SEM. Percent suppression was calculated as:

$$\% \text{ Suppression} = 1 - \frac{\text{compound treated} - \text{negative control}}{\text{positive control} - \text{negative control}} \times 100$$

Compounds (prepared in 0.25% Methocel®) were administered orally. Control animals received only vehicle (0.25% Methocel®). Negative controls were not sensitized on days 0 and 1 but were ear challenged on day 5. Ten mice are typically used per group.

Contact sensitivity results for representative compounds of the present invention are shown in Table B. In this table, + designates greater than 30% suppression of control ear swelling.

TABLE B

| Compound | Contact Sensitivity Activity |
| --- | --- |
| cyclosporin | + |
| methotrexate | + |
| Ex. 1 | + |
| Ex. 2 | + |
| Ex. 4 | + |
| Ex. 6 | + |
| Ex. 7 | + |
| Ex. 10 | + |
| Ex. 12 | + |
| Ex. 46 | + |

TABLE B-continued

| Compound | Contact Sensitivity Activity |
|---|---|
| Ex. 47 | + |
| Ex. 75 | + |

Results of the biological tests shown above demonstrate that the carbocyclic and heterocyclic quinolinecarboxylic acid compounds of Formula I of the present invention have the effect of suppressing or inhibiting the contact sensitivity response to 2,4-dinitrofluorobenzene (DNFB) in mice.

Adjuvant-Induced Arthritis

Rat adjuvant-induced arthritis represents a systemic inflammatory disease with bone and cartilage changes similar to that observed in rheumatoid arthritis, but in an accelerated time span (Pearson, *Arth. Rheum.* 7:80, 1964). Activity of test compounds in the adjuvant-induced arthritis model is indicative of anti-inflammatory activity for the treatment of chronic inflammatory diseases such as rheumatoid arthritis, psoriasis, and inflammatory bowel disease.

Male Lewis rats (Charles River) weighing 160–210 grams are injected subcutaneously with 0.1 mL of Freund's complete adjuvant containing 5 mg of M. butyricum/mL of paraffin oil (Difco Laboratories) into the plantar region of the right hind paw. Paraffin oil is injected for non-arthritic controls. Ten rats are typically used per group. Compounds are prepared in 0.25% Methocel® (Dow Chemical Company) with one drop of Tween®80 per 10 mL of Methocel®. Animals are dosed every day beginning on the day of paw injection until day 18. The weight of each animal is recorded every other day beginning on the day of the paw injections. On day 18 the animals are weighed, and the non-injected hind paw volume is measured using a Ugo Basile Volume Differential Plethysmometer.

TPA-Induced Hyperproliferation

The TPA-induced hyperproliferation test described below may be used to establish that the compounds of the present invention have the ability to inhibit skin hyperplasia induced by the repeated application of tetradecanoyl phorbol acetate (TPA) to mouse ears (Marks et al., *Cancer Res.*, 36:2636, 1976). TPA is known to induce changes in murine skin which mimics many of the inflammatory and epithelial changes which occur in human skin diseases such as psoriasis.

CF-1 male mice (Charles River; weight: 20–25 g) are treated orally with test compound prepared in 0.25% Methocel® (Dow Chemical Co.) one hour prior to the application of 1 ug of TPA (in acetone) to the right ear with acetone only to the left ear. This treatment is repeated once a day for a total of 4 consecutive days. On day 5, the animals are injected intraperitoneally with 2 mg/kg of vinblastine sulfate to arrest dividing cells in metaphase. Four hours later, the animals are sacrificed and the ears removed for histological processing. The histological slides are then examined in a light microscope and the metaphase figures per millimeter basement membrane counted. Ten mice are typically used per group.

The test results may be used to show that the compounds described herein effectively suppress the mitotic activity associated with mouse skin hyperplasia induced by TPA, indicative of efficacy in treating human skin and mucoepithelial diseases such as psoriasis (in all its forms), lichen, chronic eczema, icthyosis, pityriasis and chronic uricaria.

Anti-cancer Activity

Representative compounds of the present invention may be tested in a variety of pre-clinical animal tumor models of anti-cancer activity, described below, which are indicative of clinical utility. The anti-tumor activity may also be tested in the in vitro cell growth inhibitory assay described below.

In Vitro Growth Inhibitory Activity

The reagents for tissue culture are purchased from GIBCO (Grand Island, N.Y.). 5-(Dimethylthiazol-2-yl)-2,5-diphenyl tetrazolium bromide (MTT) was purchased from Sigma Chemical Company (St. Louis, Mo.). All agents are prepared as 2 mg/mL stock solutions in DMSO. MTT is prepared as a 1mg/mL stock solution in Dulbecco's phosphate buffered saline (PBS). All stocks are stored frozen in the dark at −20° C.

Clone A human colon cancer cells were isolated from the heterogeneous DLD-1 colon tumor line and maintained as previously described (Dexter et al. *Cancer Research* 1979, 39, 1020; Dexter et al. *Am. J. Med.* 1981, 71, 949). Murine leukemia L1210 cells are maintained in RPMI-L medium as described (Chen et al. *Cancer Research* 1986, 46, 5014). All cell lines are incubated at 37° C. in a humidified atmosphere of 5% $CO_2$–95% air.

Exponentially growing L1210 cells ($1 \times 10^3$), or Clone A cells ($8 \times 10^2$) in 0.1 mL medium are seeded in a 96-well microtiter plate on day 0. On day one, 0.1 mL aliquots of medium containing graded concentrations of test compounds are added to the cell plates. After incubation at 37° C. in a humidified incubator for 72 h, the plates containing L1210 cells are centrifuged briefly and 100 uL of the growth medium is removed. Cell cultures are incubated with 50 uL of MTT for 4 h at 37° C. The resulting purple formazan precipitate is solubilized with 200 uL of 0.04N HCl in isopropyl alcohol. Absorbance is read in a Titertek Multiskan MCC scanning well spectrophotometer (Flow Laboratories) at a test wavelength of 570 nm and a reference wavelength of 630 nm. $IC_{50}$ values are determined by a computer program that fits the data to the following equation:

$$y = ((A_m - A_o)/(1 + (X/IC_{50})^n)) + A_o$$

where $A_m$ = absorbance of the control cells; $A_o$ = absorbance of the cells in the presence of highest compound concentration; Y= observed absorbance; X= compound concentration; $IC_{50}$ dose of compound that inhibits the number of population doublings of cells to one half that of the number of population doublings of the control cells; and n equals the slope of the straight portion of the curve.

Animal Tumor Models

In the animal tumor models described below the anti-tumor activity of the compounds of the present invention may be assessed using one or more of the parameters described below.

In the tumor growth inhibition assay the efficacy of test compounds is determined by the extent of tumor growth inhibition in treated versus vehicle-treated control mice. Tumor weights (mg) are estimated from caliper measurements, using the formula for a prolate ellipsoid (mg of tumor weight= (length× width$^2$)/2). Net tumor weights are calculated for each of the treated groups and the vehicle-treated control group by subtracting the initial tumor weight from the final tumor weight when the experiment is terminated. Results are expressed using the formula:

$$\% \text{ Tumor Growth Inhibition} = \left[ 1 - \frac{\text{Mean tumor weight of treated}}{\text{Mean tumor weight of control}} \right] \times 100$$

In survival studies the anti-tumor activity is expressed using the formula:

$$\% \text{ T/C (survival)} = \frac{[\text{Mean survival time of treated}]}{[\text{Mean survival time of controls}]} \times 100$$

In tumor growth delay assays the T/C value is calculated as the median time (days) required for the treated group to reach a predetermined size (750 mg) divided by the median time required for the control group tumors to reach the same predetermined size:

% T/C (tumor growth delay) =

$$\frac{\text{[Mean time for treated group to reach tumor size]}}{\text{[Mean time for untreated group to reach tumor size]}} \times 100$$

In some cases tumor growth delay is expressed in "days" calculated by subtracting the median time in days for control group tumors to reach a predetermined weight from the median time for treated group tumors to grow to the same predetermined weight.

In experiments using mouse leukemia models, the activity of test compound may also be expressed as the percent increase in host life span (% ILS) using the formula:

% ILS=

[mean survival time treated grp– mean survival time control grp]/[mean survival time control group]×100

For subcutaneously growing tumors, the tumor cell kill is calculated as follows:

$$\text{Log}_{10} \text{ kill (total)} = \frac{[T - C \text{ (days)}]}{(3.32)(TD)}$$

where T—C is the tumor growth delay and TD is the tumor doubling time in days.

In the tumor models described below there are usually 5–10 mice per group of animals.

B16 Melanoma Model: The B16 tumor line arose spontaneously on the skin at the base of the ear in a C57BL mouse (NIH Publication No. 84-2635, February, 1984, In Vivo Cancer Models). The tumor line is maintained subcutaneously (s.c.) by serial passage in female C57BL mice. For testing, on day 0, female B6C3F1 mice weighing 18–22 g are inoculated intraperitoneally with 0.25 mL of the 1:5 tumor brei. Mice are randomized into groups. A 0.25% Methocel®/2% Tween®80 vehicle is used for control and compound formulation. Test compounds and vehicle control are administered intraperitoneally once daily for nine consecutive days beginning on day 1.

P388 Leukemia Model: The P388 tumor line originated in a lymphocyte leukemia in a female DBA/2 mouse after painting the skin with 3-methylcholanthrene (NIH Publication No. 84-2635, February, 1984, In Vivo Cancer Models). The tumor line is maintained by serial passage in female DBA/2 mice. For testing, on day 0, female CDF1 mice weighing 18–22 g are inoculated i.p. with 1×10$^6$ viable P388 cells harvested from the ascites of passage DBA/2 mice. The mice are randomized into groups. Vehicle control and test compounds are administered i.p. or i.v. once daily for five or nine consecutive days beginning on day 1 (route and days predetermined). A 0.25% Methocel®/2% Tween®80 vehicle was used for control and compound formulation.

L1210 Leukemia Model: The L1210 tumor line was originally chemically induced in 1948 in the spleen and lymph nodes of a DBA mouse by painting the skin with methylcholanthrene in ethyl ether (NIH Publication No. 84–2635, February 1984: In Vivo Cancer Models). The tumor line is maintained by serial passage in female DBA/2 mice. For testing, on day 0, female CDF1 mice weighing 18–22 g are inoculated i.p. with 1×10$^5$ L1210 cells (0.1 mL/mouse) harvested from the ascites of DBA/2 mice. The mice are randomized into groups. Vehicle control and test compounds are administered i.p. or i.v. once daily for five or nine consecutive days beginning on day 1 (route and days predetermined). A 0.25% Methocel®/2% Tween®80 vehicle is used for control and compound formulation.

Pancreatic Ductile Adenocarcinoma (Panc02 and Panc03): The pancreatic ductal adenocarcinoma tumor line originated from a tumor induced by implant of thread carrying 3-methylcholanthrene into the pancreas tissue of a mouse (Corbett et al., *Cancer Research* (1984) 44: 717–726). Tumor fragments are implanted s.c. bilaterally by trocar and the test compounds are administered i.v., p.o., or s.c. beginning 1–3 days after implantation, on a once or twice daily schedule.

Mouse Mammary AdenocarCinoma 16/C (Man16/C: The mouse mammary adenocarcinoma 16/C was originally isolated and maintained in a serial passage by transplantation of metastatic lung loci (Corbett et al., *Cancer Treat. Rep.* (1978) 62:1471–1488). Tumor fragments are implanted s.c. bilaterally by trocar and 1–3 days later treatment with test compounds begins. Compounds are administered once or twice daily. Tumors are measured with calipers once or twice weekly. Mice are sacrificed when tumors in the control group exceed an average weight of 1,500 mg.

Mouse Mammary Adenocarcinoma 17(Mam17): This tumor line is maintained in the Developmental Therapeutics Program frozen repository, maintained by the Biological Testing Branch, Frederick, Md. (Mucci-LoRusso et al., *Investigational New Drugs* (1990) 8(3): 253–261). Chemotherapeutic studies in C3H female mice bearing Mam17 tumors are conducted in the same manner as described above for the Mam16/C tumor.

Subcutaneously-implanted Colon 38 Carcinoma (Colon 38) and Colon 51 Carcinoma (Colon51): These tumor lines originated from a tumor chemically induced in the colon of C57BL/6 mouse, induced by repeated s.c. injections of 1,2-dimethylhydrazine (Corbett et al., *Cancer Research* (1975) 35:2434–2439). Tumor fragments are implanted bilaterally s.c. by trocar and 1–3 days after implantation treatment with test compound is started. Compounds are administered once or twice daily. Tumors are measured with calipers once or twice weekly until tumors in the control group exceed an average weight of 1,500 mg.

In Vivo Human Tumor Xenograft Models (MX-1,LX-1, CX-1, and DLD-2)

The MX-1 human mammary carcinoma, LX-1 human lung carcinoma, and CX-1 and DLD-2 human colon carcinoma were originally obtained from a surgically removed primary breast tumor, lung tumor, and colon carcinomas, respectively. The human tumor lines are maintained by serial passage in athymic nude mice. The MX-1 human mammary carcinoma is an established tumor used by the NCI. The MX-1 and DLD-2 tumor models have been well characterized.

The mice used may be outbred Swiss mice or BALB/c mice bearing the nude (nu/nu) gene. On day 0, 30–60 tumor fragments are implanted subcutaneously bilaterally by trocar in female mice (20–25 g). Tumor fragments are prepared from fresh tumors grown subcutaneously in passage mice. Palpable tumors weighing approximately 50 mg appear in the mice within 7–10 days after inoculation. The mice grouped and the test compounds and vehicle control are administered intravenously (i.v.) once daily on days 3, 5,7, and 12–16.

Tumor measurements and body weights are recorded once or twice a week. Mice are sacrificed when tumors reach an average weight of 1,500 mg (about day 20).

The efficacy of the test compounds is measured as the % Tumor Growth Inhibition. The criteria of the National Cancer Institute for activity in the in vivo cancer models were used (NIH Publication No. 84-2635, February 1984: In Vivo Cancer Models). Actual tumor regressions (IR= incomplete regression; FR= full regression) indicate excellent to outstanding activity. Tumor growth inhibition greater or equal to 90% is considered good to excellent and inhibition of 58–89% is considered moderate to good. Compounds demonstrating <58% growth inhibition are considered inactive.

Dosage and Formulation

The compounds of the invention can be administered to treat or prevent organ transplantation rejection, graft versus host disease, psoriasis, autoimmune diseases and chronic inflammatory diseases, by any means that produces contact of the active agent with the agent's site of action in the body of a mammal. The compounds of the present invention can also be administered to treat skin and muco-epithelial diseases such as psoriasis (in all its forms), lichen, chronic eczema, icthyosis, pityriasis and chronic uticaria. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

Suitable pharmaceutical carriers and methods of preparing pharmaceutical dosage forms are described in *Remington's Pharmaceutical Sciences*, Mack Publishing Company, a standard reference text in this field.

As is appreciated by a medical practitioner skilled in the art, the dosage administered will vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. By way of general guidance, a daily dosage of active ingredient can be about 0.1 to 100 milligrams per kilogram of body weight. Originally 0.5 to 50, and preferably 1 to 25 milligrams per kilogram per day given in divided doses 1 to 6 times a day or in sustained release form is effective to obtain desired results.

Pharmaceutical compositions (dosage forms) suitable for internal administration contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms. It can also be administered by inhalation in the form of a nasal spray or lung inhaler. It can also be administered topically as an ointment, cream, gel, paste, lotion, solution, spray, aerosol, liposome, or patch. Dosage forms used to administer the active ingredient usually contain suitable carriers, diluents, preservatives, or other excipients, as described in *Remington's Pharmaceutical Sciences*, Mack Publishing Company, a standard reference text in the field. Gelatin capsules contain the active ingredient and powdered carriers, such as lactose, sucrose, mannitol, starch, cellulose derivatives, magnesium stearate, stearic acid, and the like. Similar diluents can be used to make compressed tablets and powders. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents, and if necessary, buffer substances. Anti-oxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

The topical ointments, creams, gels, and pastes can contain diluents such as waxes, paraffins, starch, polyethylene glycol, silicones, bentonites, silicic acid, animal and vegetable fats, talc and zinc oxide or mixtures of these or other diluents. Topical solutions and emulsions can, for example, contain the customary diluents (with the exclusion of solvents having a molecular weight below 200 except in the presence of a surface-active agent), such as solvents, dissolving agents and emulsifiers; specific examples are water, ethanol, 2-propanol, ethyl carbonate, benzyl alcohol, propylene glycol, oils, glycerol, and fatty acid esters of sorbitol or mixtures thereof. Compositions for topical dosing may also contain preservatives or antioxidizing agents. The compounds of the present invention can be administered in a topical dosage form in combination with steroid drugs, particularly topical steroids such as Synalar (fluocinolone acetonide), Lidex (fluocinolone), Westcort (hydrocortisone valerate), Valisone (betamethasone valeate), and Diprasone (betamethasone dipropionate).

Powders and sprays can contain the usual diluents, such as lactose, talc, silicic acid, aluminum hydroxide, calcium silicate, and polyamide powders or mixtures of these materials. Aerosol sprays can contain the usual propellants. Liposomes can be made from such materials as animal or vegetable fats which will form lipid bilayers in which the active ingredient can be incorporated.

Patches can be made of a matrix such as polyacrylamide, and a semipermeable membrane made from a suitable polymer to control the rate at which the material is delivered to the skin.

Examples of useful pharmaceutical compositions (dosage forms) for administration of the compounds of this invention are provided below.

Capsules: Capsules may be prepared by filling standard two-piece hard gelatin capsules each with 50 mg of powdered active ingredient, 175 mg of lactose, 24 mg of talc, and 6 mg of magnesium stearate.

Soft Gelatin Capsules: A mixture of active ingredient in soybean oil is prepared and injected by means of a positive displacement pump into gelatin to form soft gelatin capsules containing 50 mg of the active ingredient. The capsules are washed in petroleum ether and dried.

Tablets: Tablets may be prepared by conventional procedures so that the dosage unit is 50 mg of active ingredient, 6 mg of magnesium stearate, 70 mg of microcrystalline cellulose, 11 mg of cornstarch, and 225 mg of lactose. Appropriate coatings may be applied to increase palatability or delay absorption.

Suspension: An aqueous suspension is prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable: A parenteral composition suitable for administration by injection is prepared by stirring 1.5% by weight of active ingredient in 10% by volume propylene glycol and water. The solution is sterilized by commonly used techniques.

Nasal Spray: An aqueous solution is prepared such that each 1 mL contains 10 mg of active ingredient, 1.8 mg methylparaben, 0.2 mg propylparaben and 10 mg methylcellulose. The solution is dispensed into 1 mL vials.

Lung Inhaler: A homogeneous mixture of the active ingredient in polysorbate 80 is prepared such that the final concentration of the active ingredient will be 10 mg per container and the final concentration of polysorbate 80 in the container will be 1% by weight. The mixture is dispensed into each can, the valves are crimped onto the can and the required amount of dichlorotetrafluoroethane is added under pressure.

Ointment: The active ingredient is added to a mixture of 48% by weight white petrolatum, 10% liquid petrolatum, 8% glycerol monostearate, 3% isopropyl myristate, and 20% lanolin at 70° C. After thorough mixing, a warm solution of methyl- and propyl-parabens in water containing sodium acetone bisulfite is added such that the final concentrations of each paraben is 0.15%, of water is 8%, and of sodium acetone bisulfite is 0.5%. The mixture is stirred until it has reached room temperature.

Topical Formulations: An ointment for topical administration may also be prepared at 70° C. by adding the active ingredient to a mixture of 48% by weight white petrolatum, 10% liquid petrolatum, 8% glycerol monostearate, 3% isopropyl myristate and 20% lanolin. After thorough mixing, a warm solution of methyl and propyl parabens in water containing sodium acetone bisulfite is added such that the final concentrations of each paraben is 0.15%, of water is 8% and of sodium acetone bisulfite is 0–5%. The mixture is stirred until it has reached room temperature.

A cream for topical administration is prepared at 75° C. by adding the active ingredient to a mixture of 1% sodium lauryl sulfate, 12% propylene glycol, 25% stearyl alcohol, 25% white petrolatum and 37% water. The mixture is stirred until it congeals.

A gel for topical administration is prepared at 70° C. by adding the active ingredient to a mixture of 0.75% Carbopol 940 (polycarbopol), 46.25% water, 3% emulsifier hydroxylated lanolin, 50% ethanol and, optionally, 1–2% diisopropylamine. The mixture is stirred until it cools to room temperature.

Pharmaceutical kits which comprise a therapeutically effective amount of a pharmaceutical composition comprising a compound of Formula I in one or more sterile containers, are also within the ambit of the present invention. Sterilization of the container may be carried out using conventional sterilization methodology well known to those skilled in the art. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the therapeutic agent to be administered, guidelines for administration, and/or guidelines for mixing the components, may also be included in the kit.

The compounds of Formula I (component (i)) can be administered in combination with a second immunosuppressive agent (component (ii)) as a combination treatment by any conventional means available for the use in conjunction with pharmaceuticals, either as individual separate dosage units administered simultaneously or concurrently, or in a physical combination of each component therapeutic agent in a single or combined dosage unit.

Such second immunosuppressive agent (component (ii)) may be selected from the group consisting of, but not limited to: cyclosporin A, azathioprine, corticosteroids such as prednisone, OKT3, FK506, mycophenolic acid or the morpholine ethyl ester thereof, 15-deoxyspergulin, rapamycin, mizoribine, misoprostol and anti-interleukin-2 (IL-2) receptor antibodies. The combination treatment can be administered to treat immuno-modulatory disorders and inflammatory diseases and particularly to prevent or treat organ transplantation rejection, graft versus host disease, psoriasis, rheumatoid arthritis, autoimmune diseases, and chronic inflammatory diseases, and related disorders, by any means that produces contact of the active ingredient(s) with the agent's site of action in the body of a mammal.

As discussed above, the dosage administered in the combination treatment will vary depending on their use and known factors such as the pharmacodynamic characteristics of the particular agent, and its mode and route of administration; age, health, and weight of the recipient; nature and extent of symptoms, kind of concurrent treatment, frequency of treatment, and the effect desired.

By way of general guidance, usually a daily oral dosage of each active ingredient can be about 0.001 to 1000 mg/kg of body weight. Ordinarily a dose of 0.1 to 100 mg/kg per day in divided doses one to six times a day or in sustained release form may be effective to obtain the desired results.

The active ingredients in the combination therapy can be administered in various dosage forms, optionally with a pharmaceutical carrier, and different dosage routes as discussed above for the single agent therapy.

The component (i) and (ii) of the invention may be formulated together, in a single dosage unit (that is, combined together in one capsule, tablet, powder, or liquid, etc.) as a combination product. When component (i) and (ii) are not formulated together in a single dosage unit, the compound of Formula I (component (i)) may be administered at the same time as the second immunosuppressive agent (component (ii)) or in any order; for example component (i) of this invention may be administered first, followed by administration of component (ii), or they may be administered in the reverse order. When not administered at the same time, preferably the administration of component (i) and (ii) of this invention occurs less than about one hour apart. Preferably, the route of administration of component (i) and (ii) of the invention is oral. The terms oral agent, oral inhibitor, oral compound, or the like, as used herein, denote compounds which may be orally administered. Although it is preferable that component (i) and component (ii) of the invention are both administered by the same route (that is, for example, both orally) or dosage form, if desired, they may each be administered by different routes (that is, for example, one component of the combination product may be administered orally, and another component may be administered intravenously) or dosage forms.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (i) and (ii) in this invention will be readily ascertainable by a medical practitioner skilled in the art, based upon the present disclosure. By way of general guidance, typically a daily dosage may be about 100 milligrams to about 1 gram of each component. By way of general guidance, when the compounds of component (i) and component (ii) are administered in combination, the dosage amount of each component may be reduced by about 70–80% relative to the usual dosage of the component when it is administered alone as a single agent.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxpropyl methylcellulose or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Representative compounds of the invention useful for the treatment of transplantation rejection, graft versus host disease, psoriasis, autoimmune diseases and inflammatory diseases are listed in Tables 1 and 2 (supra).

What is claimed is:
1. A compound of Formula I

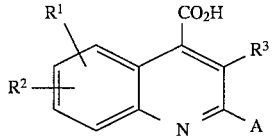

or pharmaceutically acceptable salts or prodrug forms thereof wherein:

A is selected from:

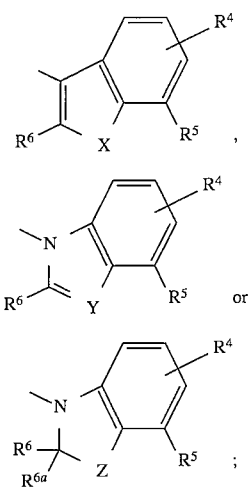

X is $-N(R^7)-$, $-O-$, $-S-$, or $-CH=CH-$; Y is $-N-$ or $-C(R^8)-$;
Z is $-C(R^8)(R^9)-$;
$R^1$ and $R^2$ are independently selected from H, Cl, Br, F, $CF_3$, or $C_1-C_4$ alkyl;
$R^3$ is selected from hydrogen, $C_1-C_3$ alkyl, $-CN$, $-NR^8R^9$, $-OR^8$, $-SR^8$, $-CF_3$, $-OCF_3$, $-SCF_3$;
$R^4$ is selected from hydrogen, Cl, F, $C_1-C_3$ alkyl, 13 $OR^{8a}$, $-CF_3$, $-OCF_3$, $-SR^{8a}$, $-SCF_3$, $-NR^8R^9$;
$R^5$ is an aryl or heteroaryl selected from phenyl, thienyl, furyl, pyridinyl, thiazolyl, or oxazolyl, said aryl or heteroaryl being optionally substituted with 0–2 $R^{11}$;
$R^6$ and $R^{6a}$ are independently selected from hydrogen or $C_1-C_3$ alkyl;
$R^7$, $R^8$, and $R^9$ are independently selected from hydrogen or $C_1-C_3$ alkyl;
$R^{8a}$ is $C_1-C_3$ alkyl;
$R^8$ and $R^9$ can alternatively join to form $-(CH_2)_4-$, $-(CH_2)_5-$, $-CH_2CH_2N(R^{10})CH_2CH_2-$, or $-CH_2CH_2OCH_2CH_2-$;
$R^{10}$ is hydrogen or methyl;
$R^{11}$ is selected from hydrogen, Cl, F, $C_1-C_3$ alkyl, $-OR^{8a}$, $-CF_3$, $-OCF_3$, $-SR^{8a}$, $-SCF_3$, $-NR^8R^9$.

2. A compound of claim 1 of Formula II:

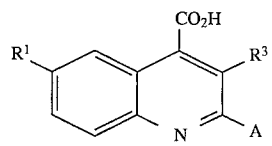

or a pharmaceutically acceptable salt form thereof, wherein:
X is $-NR^7-$ or $-CH=CH-$;
Y is $-C(R^8)-$.or$-N-$;
Z is $-C(R^8)(R^9)-$
$R^1$ is F or $CF_3$;
$R^3$ is hydrogen or methyl;
$R^4$ is hydrogen;
$R^5$ is phenyl substituted with 0–2 $R^{11}$;
$R^6$ and $R^{6a}$ are both hydrogen;
$R^8$ is H or $CH_3$;
$R^{11}$ is hydrogen, methyl, $-OCH_3$, $-F$ or $-CF_3$.

3. A compound of claim 2, or a pharmaceutically acceptable salt form thereof, wherein:
   $R^5$ is phenyl, 2-methylphenyl, 2-fluorophenyl, 2-methoxyphenyl, 3-methoxyphenyl or 3-trifluoromethylphenyl.

4. A compound of claim 1, or a pharmaceutically acceptable salt thereof, selected from the following:
   6-fluoro-3-methyl-2-(4-phenyl-1-indolinyl)-quinoline-4-carboxylic acid, sodium salt,
   6-fluoro-2-[4-(2-fluorophenyl)-1-indolinyl]-3-methylquinoline- 4-carboxylic acid, sodium salt,
   6-fluoro-[4-(2-methoxyphenyl)-1-indolinyl]-3-methylquinoline-4-carboxylic acid, sodium salt,
   6-fluoro-3-methyl-2-[4-(2-methylphenyl)-1-indolinyl]-quinoline-4-carboxylic acid, sodium salt,
   6-fluoro-[4-(3-methoxyphenyl)-1-indolinyl]-3-methylquinoline-4-carboxylic acid, sodium salt,
   6-fluoro-3-methyl-2-[4-(3-trifluoromethylphenyl)-1-indolinyl ]-quinoline-4-carboxylic acid, sodium salt,
   6-fluoro-2-(4-phenyl-1-indolinyl)-quinoline-4-carboxylic acid, sodium salt,
   6-fluoro-2-[4-(2-methylphenyl)-1-indolinyl]-quinoline-4-carboxylic acid, sodium salt,
   6-fluoro-2-[4-(3-trifluoromethylphenyl)-1-indolinyl]-quinoline- 4-carboxylic acid, sodium salt,
   6-fluoro-3-methyl-2-(4-phenyl-1-indolyl)-quinoline-4-carboxylic acid, sodium salt,
   6-fluoro-3-methyl-2-(4-phenyl-1-indolinyl)-quinoline-4-carboxylic acid, diethanolamine salt,
   6-fluoro-3-methyl-2-(4-phenyl-1-indolinyl)-quinoline-4-carboxylic acid, N-methyl-D-glucamine salt,
   6-fluoro-3-methyl-2-(4-phenyl-1-indolinyl)-quinoline-4-carboxylic acid, procaine salt,
   6-fluoro-3-methyl-2-(4-phenyl-1-indolinyl)-quinoline-4-carboxylic acid, lysine salt,
   6-fluoro-3-methyl-2-(4-phenyl-1-indolinyl)-quinoline-4-carboxylic acid, choline salt,
   6-fluoro-3-methyl-2-(4-phenyl-1-indolinyl)-quinoline-4-carboxylic acid, tris-(hydroxymethyl)aminomethane salt,
   6-fluoro-3-methyl-2-(5-phenyl-1-naphthyl)-quinoline-4-carboxylic acid, sodium salt,
   6-fluoro-3-methyl-2-(7-phenyl-1-methyl-3-indolyl)-quinoline- 4-carboxylic acid, sodium salt,
   3-methyl-2-(7-phenyl-1-methyl-3-indolyl)-6-trifluoromethylquinoline-4-carboxylic acid, sodium salt,
   6-fluoro-3-methyl-2-(6-fluoro-4-phenyl-1-benzimidazolyl)-quinoline-4-carboxylic acid.

5. A pharmaceutical composition comprising a compound of claim 1 and a pharmaceutically acceptable carrier.

6. A pharmaceutical composition comprising a compound of claim 2 and a pharmaceutically acceptable carrier.

7. A pharmaceutical composition comprising a compound of claim 3 and a pharmaceutically acceptable carrier.

8. A pharmaceutical composition comprising a compound of claim 4 and a pharmaceutically acceptable carrier.

* * * * *